US008613742B2

(12) United States Patent
Suslov

(10) Patent No.: US 8,613,742 B2
(45) Date of Patent: Dec. 24, 2013

(54) METHODS OF SEALING VESSELS USING PLASMA

(75) Inventor: Nikolay Suslov, Vastra Frolonda (SE)

(73) Assignee: Plasma Surgical Investments Limited, Tortola (VG)

( * ) Notice: Subject to any disclaimer, the term of this patent is extended or adjusted under 35 U.S.C. 154(b) by 792 days.

(21) Appl. No.: 12/696,411

(22) Filed: Jan. 29, 2010

(65) Prior Publication Data

US 2011/0190752 A1 Aug. 4, 2011

(51) Int. Cl.
*A61B 18/04* (2006.01)

(52) U.S. Cl.
USPC .................................. 606/27; 606/26; 606/41

(58) Field of Classification Search
USPC ...................................................... 606/40–49
See application file for complete search history.

(56) References Cited

U.S. PATENT DOCUMENTS

| 3,077,108 A | 2/1963 | Gage et al. |
| 3,082,314 A | 3/1963 | Yoshiaki et al. |
| 3,100,489 A | 8/1963 | Bagley |
| 3,145,287 A | 8/1964 | Seibein et al. |
| 3,153,133 A | 10/1964 | Ducati |
| 3,270,745 A | 9/1966 | Wood |
| 3,360,988 A | 1/1968 | Stein et al. |
| 3,413,509 A | 11/1968 | Cann et al. |
| 3,433,991 A | 3/1969 | Whyman |
| 3,434,476 A | 3/1969 | Shaw et al. |
| 3,534,388 A | 10/1970 | Takakiyo et al. |
| 3,628,079 A | 12/1971 | Dobbs et al. |
| 3,676,638 A | 7/1972 | Stand |
| 3,775,825 A | 12/1973 | Wood et al. |
| 3,803,380 A | 4/1974 | Ragaller |
| 3,838,242 A | 9/1974 | Goucher |
| 3,851,140 A | 11/1974 | Coucher |
| 3,866,089 A | 2/1975 | Hengartner |
| 3,903,891 A | 9/1975 | Brayshaw |
| 3,914,573 A | 10/1975 | Muehlberger |
| 3,938,525 A | 2/1976 | Goucher |
| 3,991,764 A | 11/1976 | Incropera et al. |
| 3,995,138 A | 11/1976 | Kalev et al. |

(Continued)

FOREIGN PATENT DOCUMENTS

| AU | 2000250426 | 6/2005 |
| AU | 2006252145 | 1/2007 |

(Continued)

OTHER PUBLICATIONS

Office Action of U.S. Appl. No. 11/482,582, dated Dec. 6, 2010.

(Continued)

*Primary Examiner* — Linda Dvorak
*Assistant Examiner* — Amanda Scott
(74) *Attorney, Agent, or Firm* — Jones Day

(57) ABSTRACT

A method for sealing fluid-carrying vessels in a living organism using high temperature plasma is disclosed. A flow rate of 0.25-0.5 L/min of room-temperature plasma generating gas and the initial temperature of the discharged plasma of 12.5-15.5 kK ensure a laminar plasma flow and its ability to penetrate into the vessel. The plasma flow is directed into the vessel, where it keeps a portion of the vessel free of liquid. Heat is transferred to the vessel walls, and the denaturing of collagen in the vessel walls causes the walls to contract until complete occlusion occurs. The method may be used with devices adapted for tissue dissection and coagulation.

21 Claims, 27 Drawing Sheets

(56) References Cited

U.S. PATENT DOCUMENTS

| | | |
|---|---|---|
| 4,029,930 A | 6/1977 | Sagara et al. |
| 4,035,684 A | 7/1977 | Svoboda et al. |
| 4,041,952 A | 8/1977 | Morrison, Jr. et al. |
| 4,201,314 A | 5/1980 | Samuels et al. |
| 4,256,779 A | 3/1981 | Sokol et al. |
| 4,317,984 A | 3/1982 | Fridlyand |
| 4,397,312 A | 8/1983 | Molko |
| 4,445,021 A | 4/1984 | Irons et al. |
| 4,620,080 A | 10/1986 | Arata et al. |
| 4,661,682 A | 4/1987 | Gruner et al. |
| 4,672,163 A | 6/1987 | Matsui et al. |
| 4,674,683 A | 6/1987 | Fabel |
| 4,682,598 A | 7/1987 | Beraha |
| 4,696,855 A | 9/1987 | Pettit et al. |
| 4,711,627 A | 12/1987 | Oeschsle et al. |
| 4,713,170 A | 12/1987 | Saibic |
| 4,743,734 A | 5/1988 | Garlanov et al. |
| 4,764,656 A | 8/1988 | Browning |
| 4,777,949 A | 10/1988 | Perlin |
| 4,780,591 A | 10/1988 | Bernecki et al. |
| 4,781,175 A | 11/1988 | McGreevy et al. |
| 4,784,321 A | 11/1988 | Delaplace |
| 4,785,220 A | 11/1988 | Brown et al. |
| 4,839,492 A | 6/1989 | Bouchier et al. |
| 4,841,114 A | 6/1989 | Browning |
| 4,853,515 A | 8/1989 | Willen et al. |
| 4,855,563 A | 8/1989 | Beresnev et al. |
| 4,866,240 A | 9/1989 | Webber |
| 4,869,936 A | 9/1989 | Moskowitz et al. |
| 4,874,988 A | 10/1989 | English |
| 4,877,937 A | 10/1989 | Muller |
| 4,916,273 A | 4/1990 | Browning |
| 4,924,059 A | 5/1990 | Rotolico et al. |
| 5,008,511 A | 4/1991 | Ross |
| 5,013,883 A | 5/1991 | Fuimefreddo et al. |
| 5,100,402 A | 3/1992 | Fan |
| 5,144,110 A | 9/1992 | Marantz et al. |
| 5,151,102 A | 9/1992 | Kamiyama et al. |
| 5,201,900 A | 4/1993 | Nardella |
| 5,207,691 A | 5/1993 | Nardella |
| 5,211,646 A | 5/1993 | Alperovich et al. |
| 5,217,460 A | 6/1993 | Knoepfler |
| 5,225,652 A | 7/1993 | Landes |
| 5,227,603 A | 7/1993 | Doolette et al. |
| 5,261,905 A | 11/1993 | Doresey |
| 5,285,967 A | 2/1994 | Weidman |
| 5,332,885 A | 7/1994 | Landes |
| 5,352,219 A | 10/1994 | Reddy |
| 5,396,882 A | 3/1995 | Zapol |
| 5,403,312 A | 4/1995 | Yates et al. |
| 5,406,046 A | 4/1995 | Landes |
| 5,408,066 A | 4/1995 | Trapani et al. |
| 5,412,173 A | 5/1995 | Muehlberger |
| 5,445,638 A | 8/1995 | Rydell et al. |
| 5,452,854 A | 9/1995 | Keller |
| 5,460,629 A | 10/1995 | Shlain et al. |
| 5,485,721 A | 1/1996 | Steenborg |
| 5,514,848 A | 5/1996 | Ross et al. |
| 5,519,183 A | 5/1996 | Mueller |
| 5,527,313 A | 6/1996 | Scott et al. |
| 5,573,682 A | 11/1996 | Beason et al. |
| 5,582,611 A | 12/1996 | Tsuruta et al. |
| 5,620,616 A | 4/1997 | Anderson et al. |
| 5,629,585 A | 5/1997 | Altmann |
| 5,637,242 A | 6/1997 | Muehlberger |
| 5,640,843 A | 6/1997 | Aston |
| 5,662,680 A | 9/1997 | Desai |
| 5,665,085 A | 9/1997 | Nardella |
| 5,679,167 A | 10/1997 | Muehlberger |
| 5,680,014 A | 10/1997 | Miyamoto et al. |
| 5,688,270 A | 11/1997 | Yates et al. |
| 5,697,281 A | 12/1997 | Eggers et al. |
| 5,697,882 A | 12/1997 | Eggers et al. |
| 5,702,390 A | 12/1997 | Austin et al. |
| 5,720,745 A * | 2/1998 | Farin et al. ..................... 606/49 |
| 5,733,662 A | 3/1998 | Bogachek |
| 5,797,941 A | 8/1998 | Schulze et al. |
| 5,827,271 A | 10/1998 | Buysse et al. |
| 5,833,690 A | 11/1998 | Yates et al. |
| 5,837,959 A | 11/1998 | Muehlberger et al. |
| 5,843,079 A * | 12/1998 | Suslov ............................ 606/43 |
| 5,858,469 A | 1/1999 | Sahoo et al. |
| 5,858,470 A | 1/1999 | Bernecki et al. |
| 5,897,059 A | 4/1999 | Muller |
| 5,906,757 A | 5/1999 | Kong et al. |
| 5,932,293 A | 8/1999 | Belashchenko et al. |
| 6,003,788 A | 12/1999 | Sedov |
| 6,042,019 A | 3/2000 | Rusch |
| 6,099,523 A | 8/2000 | Kim et al. |
| 6,114,649 A | 9/2000 | Delcea |
| 6,135,998 A | 10/2000 | Palanker |
| 6,137,078 A | 10/2000 | Keller |
| 6,137,231 A | 10/2000 | Anders |
| 6,162,220 A | 12/2000 | Nezhat |
| 6,169,370 B1 | 1/2001 | Platzer |
| 6,181,053 B1 | 1/2001 | Roberts |
| 6,202,939 B1 | 3/2001 | Delcea |
| 6,273,789 B1 | 8/2001 | LaSalle et al. |
| 6,283,386 B1 | 9/2001 | Van Steenkiste et al. |
| 6,352,533 B1 | 3/2002 | Ellman et al. |
| 6,386,140 B1 | 5/2002 | Muller et al. |
| 6,392,189 B1 | 5/2002 | Delcea |
| 6,443,948 B1 | 9/2002 | Suslov et al. |
| 6,475,212 B2 | 11/2002 | Dobak, III et al. |
| 6,475,215 B1 | 11/2002 | Tanrisever |
| 6,514,252 B2 | 2/2003 | Nezhat et al. |
| 6,515,252 B1 | 2/2003 | Girold |
| 6,528,947 B1 | 3/2003 | Chen et al. |
| 6,548,817 B1 | 4/2003 | Anders |
| 6,562,037 B2 | 5/2003 | Paton et al. |
| 6,629,974 B2 | 10/2003 | Penny et al. |
| 6,657,152 B2 | 12/2003 | Shimazu |
| 6,669,106 B2 | 12/2003 | Delcea |
| 6,676,655 B2 | 1/2004 | McDaniel et al. |
| 6,780,184 B2 | 8/2004 | Tanrisever |
| 6,845,929 B2 | 1/2005 | Dolatabadi et al. |
| 6,886,757 B2 | 5/2005 | Byrnes et al. |
| 6,958,063 B1 | 10/2005 | Soll et al. |
| 6,972,138 B2 | 12/2005 | Heinrich et al. |
| 6,986,471 B1 | 1/2006 | Kowalsky et al. |
| 7,025,764 B2 | 4/2006 | Paton et al. |
| 7,030,336 B1 | 4/2006 | Hawley |
| 7,118,570 B2 | 10/2006 | Tetzlaff et al. |
| 7,589,473 B2 * | 9/2009 | Suslov ..................... 315/111.21 |
| 2001/0041227 A1 | 11/2001 | Hislop |
| 2002/0013583 A1 | 1/2002 | Camran et al. |
| 2002/0071906 A1 | 6/2002 | Rusch |
| 2002/0091385 A1 | 7/2002 | Paton et al. |
| 2002/0097767 A1 | 7/2002 | Krasnov |
| 2003/0030014 A1 | 2/2003 | Wieland et al. |
| 2003/0040744 A1 | 2/2003 | Latterell et al. |
| 2003/0075618 A1 | 4/2003 | Shimazu |
| 2003/0114845 A1 | 6/2003 | Paton et al. |
| 2003/0125728 A1 | 7/2003 | Nezhat et al. |
| 2003/0178511 A1 | 9/2003 | Dolatabadi et al. |
| 2003/0190414 A1 | 10/2003 | Van Steenkiste |
| 2004/0018317 A1 | 1/2004 | Heinrich et al. |
| 2004/0064139 A1 | 4/2004 | Yossepowitch |
| 2004/0068304 A1 | 4/2004 | Paton et al. |
| 2004/0116918 A1 | 6/2004 | Konesky |
| 2004/0124256 A1 | 7/2004 | Itsukaichi et al. |
| 2004/0129222 A1 | 7/2004 | Nylen et al. |
| 2004/0195219 A1 | 10/2004 | Conway |
| 2005/0082395 A1 | 4/2005 | Gardega |
| 2005/0120957 A1 | 6/2005 | Kowalsky et al. |
| 2005/0192610 A1 | 9/2005 | Houser et al. |
| 2005/0192611 A1 | 9/2005 | Houser |
| 2005/0192612 A1 | 9/2005 | Houser et al. |
| 2005/0234447 A1 | 10/2005 | Paton et al. |
| 2005/0255419 A1 | 11/2005 | Belashchenko et al. |
| 2006/0004354 A1 | 1/2006 | Suslov |
| 2006/0037533 A1 | 2/2006 | Belashchenko et al. |
| 2006/0049149 A1 | 3/2006 | Shimazu |
| 2006/0090699 A1 | 5/2006 | Muller |

(56) References Cited

U.S. PATENT DOCUMENTS

| | | |
|---|---|---|
| 2006/0091116 A1 | 5/2006 | Suslov |
| 2006/0091117 A1 | 5/2006 | Blankenship et al. |
| 2006/0091119 A1 | 5/2006 | Zajchowski et al. |
| 2006/0108332 A1 | 5/2006 | Belashchenko |
| 2006/0189976 A1 | 8/2006 | Karni et al. |
| 2006/0217706 A1 | 9/2006 | Lau et al. |
| 2006/0287651 A1 | 12/2006 | Bayat |
| 2007/0021747 A1 | 1/2007 | Suslov |
| 2007/0021748 A1* | 1/2007 | Suslov .......................... 606/45 |
| 2007/0029292 A1 | 2/2007 | Suslov |
| 2007/0038214 A1 | 2/2007 | Morley et al. |
| 2007/0138147 A1 | 6/2007 | Molz et al. |
| 2007/0173871 A1 | 7/2007 | Houser et al. |
| 2007/0173872 A1 | 7/2007 | Neuenfeldt |
| 2007/0191828 A1 | 8/2007 | Houser et al. |
| 2008/0015566 A1 | 1/2008 | Livneh |
| 2008/0071206 A1 | 3/2008 | Peters |
| 2008/0114352 A1 | 5/2008 | Long et al. |
| 2008/0185366 A1 | 8/2008 | Suslov |
| 2008/0246385 A1 | 10/2008 | Schamiloglu et al. |
| 2009/0039789 A1 | 2/2009 | Nikolay |
| 2009/0039790 A1 | 2/2009 | Suslov |

FOREIGN PATENT DOCUMENTS

| | | |
|---|---|---|
| CA | 983586 | 2/1979 |
| CA | 1144104 | 4/1983 |
| CA | 1308772 | 10/1992 |
| CA | 2594515 | 7/2006 |
| CN | 85107499 B | 4/1987 |
| CN | 1331836 A | 1/2002 |
| CN | 1557731 | 12/2004 |
| CN | 1682578 A | 10/2005 |
| DE | 2033072 | 2/1971 |
| DE | 10127261 | 9/1993 |
| DE | 4209005 | 12/2002 |
| EP | 0282677 | 12/1987 |
| EP | 0411170 | 2/1991 |
| EP | 0748149 | 12/1996 |
| EP | 0851040 | 7/1998 |
| EP | 1293169 | 3/2003 |
| EP | 1570798 | 9/2005 |
| ES | 2026344 | 4/1992 |
| FR | 2193299 | 2/1974 |
| FR | 2567747 | 1/1986 |
| GB | 0751735 | 7/1956 |
| GB | 0921016 | 3/1963 |
| GB | 1125806 | 9/1968 |
| GB | 1176333 | 1/1970 |
| GB | 1268843 | 3/1972 |
| GB | 2407050 | 4/2005 |
| JP | 47009252 | 3/1972 |
| JP | 52-117255 A | 10/1977 |
| JP | 54120545 | 2/1979 |
| JP | 57001580 | 1/1982 |
| JP | 57068269 | 4/1982 |
| JP | 6113600 A | 1/1986 |
| JP | A-S61-193783 | 8/1986 |
| JP | A-S61-286075 | 12/1986 |
| JP | 62123004 | 6/1987 |
| JP | 01198539 | 8/1989 |
| JP | 1-319297 A | 12/1989 |
| JP | 1319297 A | 12/1989 |
| JP | 03043678 | 2/1991 |
| JP | 06262367 | 9/1994 |
| JP | 09299380 | 11/1997 |
| JP | 10024050 | 1/1998 |
| JP | 10234744 | 9/1998 |
| JP | 10504751 | 12/1998 |
| JP | 2002541902 | 12/2002 |
| JP | 2008036001 | 2/2008 |
| JP | 2008-284580 A | 11/2008 |
| MX | 04010281 | 6/2005 |
| RU | 2178684 | 1/2002 |
| RU | 2183480 | 6/2002 |
| RU | 2183946 | 6/2002 |
| WO | WO 92/19166 | 11/1992 |
| WO | WO 96/06572 | 3/1996 |
| WO | WO 97/11647 | 4/1997 |
| WO | WO 01/62169 | 8/2001 |
| WO | WO 02/30308 | 4/2002 |
| WO | WO 03/028805 | 4/2003 |
| WO | WO 2004/028221 | 4/2004 |
| WO | WO 2004/030551 | 4/2004 |
| WO | WO 2004/105450 | 12/2004 |
| WO | WO 2005/009595 | 10/2005 |
| WO | WO 2005/099595 | 10/2005 |
| WO | WO 2006/012165 | 2/2006 |
| WO | WO 2007/003157 | 1/2007 |
| WO | WO 2007/006516 A2 | 1/2007 |
| WO | WO 2007/006517 | 1/2007 |
| WO | WO 2007/040702 | 4/2007 |

OTHER PUBLICATIONS

Office Action of U.S. Appl. No. 11/482,581, dated Dec. 8, 2010.
Notice of Allowance of U.S. Appl. No. 11/701,911, dated Dec. 6, 2010.
Japanese Office Action of application No. 2009-547536, dated Feb. 15, 2012.
Chinese Office Action of application No. 200780100857.9, dated Nov. 28, 2011 (with English translation).
International Search Report of application No. PCT/EP2010/060641, dated Apr. 14, 2011.
Written Opinion of International application No. PCT/EP2010/060641, dated Apr. 14, 2011.
Office Action of U.S. Appl. No. 13/357,895, dated Mar. 29, 2012.
Office Action of U.S. Appl. No. 11/482,580, dated Apr. 11, 2012.
Office Action of U.S. Appl. No. 13/358,934, dated Apr. 24, 2012.
Japanese Office Action of application No. 2010-519340, dated Mar. 13, 2012 (with translation).
Chinese Office Action of application No. 200780100858.3, dated Apr. 27, 2012 (with English translation).
Japanese Office Action of application No. 2010-519339, dated Apr. 3, 2012 (with English translation).
Office Action of U.S. Appl. No. 11/482,582, dated May 23, 2011.
Notice of Allowance of U.S. Appl. No. 12/557,645, dated May 26, 2011.
510(k) Summary, dated Jun. 2, 2008.
510(k) Summary, dated Oct. 30, 2003.
Aptekman, 2007, "Spectroscopic analysis of the PlasmaJet argon plasma with 5mm-0.5 coag-cut handpieces", Document PSSRP-106—K080197.
Asawanonda et al., 2000, "308-nm excimer laser for the treatment of psoriasis: a dose-response study."Arach. Dermatol. 136:619-24.
Branson, M.D., 2005, "Preliminary experience with neutral plasma, a new coagulation technology, in plastic surgery", Fayetteville, NY.
Charpentier et al., 2008, "Multicentric medical registry on the use of the Plasma Surgical PlasmaJet System in thoracic surgery", Club Thorax.
Chen et al., 2006, "What do we know about long laminar plasma jets?", Pure Appl Chem; 78(6):1253-1264.
Cheng et al., 2006, "Comparison of laminar and turbulent thermal plasma jet characteristics—a modeling study", Plasma Chem Plasma Process; 26:211-235.
CoagSafe™ Neutral Plasma Coagulator Operator Manual, Part No. OMC-2100-1, Revision 1.1, dated Mar. 2003—Appendix 1of K030819.
Coven et al., 1999, "PUVA-induced lymphocyte apoptosis: mechanism of action in psoriasis." Photodermatol. Photoimmunol. Photomed. 15:22-7.
Dabringhausen et al., 2002, "Determination of HID electrode falls in a model lamp I: Pyrometric measurements." J. Phys. D. Appl. Phys. 35:1621-1630.
Davis (ed), 2004, ASM Thermal Spray Society, Handbook of Thermal Spray Technology, U.S. 42-168.

(56) References Cited

OTHER PUBLICATIONS

Feldman et al., 2002, "Efficacy of the 308-nm excimer laser for treatment of psoriasis: results of a multicenter study." J. Am Acad. Dermatol. 46:900-6.
Gerber et al., 2003, "Ultraviolet B 308-nm excimer laser treatment of psoriasis: a new phototherapeutic approach." Br. J. Dermatol. 149:1250-8.
Gugenheim et al., 2006, "Open, muliticentric, clinical evaluation of the technical efficacy, reliability, safety, and clinical tolerance of the plasma surgical PlasmaJet System for intra-operative coagulation in open and laparoscopic general surgery", Department of Digestive Surgery, University Hospital, Nice, France.
Haemmerich et al., 2003, "Hepatic radiofrequency ablation with internally cooled probes: effect of coolant temperature on lesion size", IEEE Transactions of Biomedical Engineering; 50(4):493-500.
Honigsmann, 2001, "Phototherapy for psoriasis." Clin. Exp. Dermatol. 26:343-50.
Huang et al., 2008, "Laminar/turbulent plasma jets generated at reduced pressure", IEEE Transaction on Plasma Science; 36(4):1052-1053.
Iannelli et al., 2005, "Neutral plasma coagulation (NPC)—A preliminary report on a new technique for post-bariatric corrective abdominoplasty", Department of Digestive Surgery, University Hospital, Nice, France.
International Preliminary Report on Patentability of International application No. PCT/EP2007/006939, dated Feb. 9, 2010.
International Preliminary Report on Patentability of International application No. PCT/EP2007/006940, dated Feb. 9, 2010.
International Preliminary Report on Patentability of International application No. PCT/EP2007/000919, dated Aug. 4, 2009.
International-type Search report dated Jan. 18, 2006, Swedish App. No. 0501603-5.
International-type Search report dated Jan. 18, 2006, Swedish App. No. 0501602-7.
International-type Search Report, dated Jan. 18, 2006, Swedish App. No. 0501604-3.
Letter to FDA re: 501(k) Notification (21 CFR 807.90(e)) for the PlasmaJet® Neutral Plasma Surgery System, dated Jun. 2, 2008—K080197.
Lichtenberg et al., 2002, "Observation of different modes of cathodic arc attachment to HID electrodes in a model lamp." J. Phys. D. Appl. Phys. 35:1648-1656.
Merloz, 2007, "Clinical evaluation of the Plasma Surgical PlasmaJet tissue sealing system in orthopedic surgery—Early report", Orthopedic Surgery Department, University Hospital, Grenoble, France.
News Release and Video—2009, New Sugical Technology Offers Better Outcomes for Women's Reproductive Disorders: Stanford First in Bay Area to Offer PlasmaJet, Stanford Hospital and Clinics.
Nezhat et al., 2009, "Use of neutral argon plasma in the laparoscopic treatment of endometriosis", Journal of the Society of Laparoendoscopic Surgeons.
Notice of Allowance dated May 15, 2009, of U.S. Appl. No. 11/890,938.
Office Action dated Apr. 17, 2008 of U.S. Appl. No. 11/701,911.
Office Action dated Feb. 1, 2008 of U.S. Appl. No. 11/482,580.
Office Action dated Mar. 13, 2009 of U.S. Appl. No. 11/701,911.
Office Action dated Mar. 19, 2009 of U.S. Appl. No. 11/482,580.
Office Action dated Oct. 18, 2007 of U.S. Appl. No. 11/701,911.
Office Action dated Oct. 19, 2009 of U.S. Appl. No. 11/482,580.
Office Action dated Sep. 17, 2009 of U.S. Appl. No. 11/890,937.
Office Action dated Sep. 29, 2009 of U.S. Appl. No. 11/701,911.
Office Action dated Apr. 2, 2010 of U.S. Appl. No. 11/701,911.
Office Action dated Apr. 9, 2010 of U.S. Appl. No. 11/890,937.
Office Action dated Jun. 23, 2010 of U.S. Appl. No. 11/482,582.
Office Action dated Jun. 24, 2010 of U.S. Appl. No. 11/482,581.
Palanker et al., 2008, "Electrosurgery with cellular precision", IEEE Transactions of Biomedical Engineering; 55(2):838-841.
Pan et al., 2001, "Generation of long, laminar plasma jets at atmospheric pressure and effects of low turbulence", Plasma Chem Plasma Process; 21(1):23-35.
Pan et al., 2002, "Characteristics of argon laminar DC Plasma Jet at atmospheric pressure", Plasma Chem and Plasma Proc; 22(2):271-283.
PCT International Preliminary Report on Patentability and Written Opinion of the International Searching Authority, dated Aug. 4, 2009, International App. No. PCT/EP2007/000919.
PCT International Search Report dated Feb. 14, 2007, International App. No. PCT/EP2006/006688.
PCT International Search Report dated Feb. 22, 2007, International App. No. PCT/EP2006/006689.
PCT International Search Report dated Feb. 22, 2007, of International appl. No. PCT/EP2006/006690.
PCT Written Opinion of the International Searching Authority dated Feb. 22, 2007, International App. No. PCT/EP2006/006690.
PCT International Search Report PCT/EP2007/006939, dated May 26, 2008.
PCT International Search Report PCT/EP2007/006940.
PCT International Search Report, dated Oct. 23, 2007, International App. No. PCT/EP2007/000919.
PCT Invitation to Pay Additional Fees PCT/EP2007/006940, dated May 20, 2008.
PCT Written Opinion of the International Searching Authority PCT/EP2007/006939, dated May 26, 2008.
PCT Written Opinion of the International Searching Authority dated Oct. 23, 2007, International App. No. PCT/EP2007/000919.
PCT Written Opinion of the International Searching Authority PCT/EP2007/006940.
PCT Written Opionin of the International Searching Authority dated Feb. 14, 2007, International App. No. PCT/EP2006/006688.
PCT Written Opionin of the International Searching Authority dated Feb. 22, 2007, International App. No. PCT/EP2006/006689.
Plasma Surgical Headlines Article: Atlanta, Feb. 2, 2010—"New Facilities Open in UK and US".
Plasma Surgical Headlines Article: Atlanta, Feb. 2, 2010—"PlasmaJet to be Featured in Live Case at Endometriosis 2010 in Milan, Italy".
Plasma Surgical Headlines Article: Chicago, Sep. 17, 2008—"PlasmaJet Named Innovation of the Year by the Society of Laparoendoscopic Surgeons".
PlasmaJet English Brochure.
Plasmajet Neutral Plasma Coagulator Operator Manual, Part No. OMC-2100-1 (Revision 1.7, dated May 2004)—K030819.
Plasmajet Operator Manual Part No. OMC-2130-EN (Revision 3.1/Draft) dated May 2008—K080197.
Premarket Notification 510(k) Submission, Plasma Surgical Ltd.—PlasmaJet™ (formerly CoagSafe™) Neutral Plasma Coagulator, Additional information provided in response to the e-mail request dated Jul. 14, 2004—K030819.
Report on the comparative analysis of morphological changes in tissue from different organs after using the PlasmaJet version 3 (including cutting handpieces), Aug. 2007—K080197.
Schmitz & Riemann, 2002, "Analysis of the cathode region of atmospheric pressure discharges." J. Phys. D. Appl. Phys. 35:1727-1735.
Trehan & Taylor, 2002, "Medium-dose 308-nm excimer laser for the treatment of psoriasis." J. Am. Acad. Dermatol. 47:701-8.
U.S. Appl. No. 12/557,645; Suslov, Sep. 11, 2009.
www.plasmasurgical.com, as of Feb. 18, 2010.
Zenker, 2008, "Argon plasma coagulation", German Medical Science; 3(1):1-5.
European Office Action of application No. 07786583.0-1226, dated Jun. 29, 2010.
Office Action of U.S. Appl. No. 11/701,911 dated Jul. 19, 2010.
Chinese Office Action of application No. 200780052471.5, dated May 25, 2012 (with English translation).
Chinese Office Action of application No. 200780100857.9, dated May 25, 2012 (with English translation).
Chinese Office Action (translation) of application No. 200680030225.5, dated Jun. 11, 2010.
Chinese Office Action (translation) of application No. 200680030216.6, dated Oct. 26, 2010.

(56) References Cited

OTHER PUBLICATIONS

Chinese Office Action (translation) of application No. 200680030194.3, dated Jan. 31, 2011.
Chinese Office Action (translation) of application No. 200680030225.5, dated Mar. 9, 2011.
Japanese Office Action (translation) of application No. 2008-519873, dated Jun. 10, 2011.
Notice of Allowance and Fees Due of U.S. Appl. No. 13/358,934, dated Sep. 5, 2012.
Office Action of U.S. Appl. No. 13/357,895, dated Sep. 7, 2012.
Chinese Office Action of Chinese application No. 200780100858.3, dated Aug. 29, 2012.
Office Action of U.S. Appl. No. 11/482,580, dated Oct. 24, 2012.
Notice of Allowance and Fees Due of U.S. Appl. No. 11/482,581, Oct. 28, 2011.
Notice of Allowance and Fees Due of U.S. Appl. No. 11/482,582, Sep. 23, 2011.
Supplemental Notice of Allowability of U.S. Appl. No. 11/482,582, Oct. 12, 2011.
Supplemental Notice of Allowability of U.S. Appl. No. 11/482,582, Oct. 25, 2011.
U.S. Appl. No. 12/841,361, filed Jul. 22, 2010, Suslov.
International Search Report of International application No. PCT/EP2010/051130, dated Sep. 27, 2010.
Written Opinion of International application No. PCT/EP2010/051130, dated Sep. 27, 2010.
Severtsev et al. 1997, "Polycystic liver disease: sclerotherapy, surgery and sealing of cysts with fibrin sealant", European Congress of the International Hepatobiliary Association, Hamburg, Germany Jun. 8-12; p. 259-263.
Office Action of U.S. Appl. No. 12/557,645, dated Nov. 26, 2010.
Chinese Office Action of application No. 2007801008583, dated Oct. 19, 2011 (with English translation).
510(k) Notification (21 CFR 807.90(e)) for the Plasma Surgical Ltd. PlasmaJet® Neutral Plasma Surgery System, Section 10—Executive Summary—K080197, dated Jan. 25, 2008.
Deb et al., "Histological quantification of the tissue damage caused in vivo by neutral PlasmaJet coagulator", Nottingham University Hospitals, Queen's medical Centre, Nottingham NG7 2UH Poster, dated Oct. 2009.
Electrosurgical Generators Force FX™ Electrosurgical Generators by ValleyLab—K080197, dated Sep. 2002.
ERBE APC 300 Argon Plasma Coagulation Unit for Endoscopic Applications, Brochure 1997—Appendix 4 of K030819.
FORCE Argon™ II System, Improved precision and control in electrosurgery, by Valleylab—K080197, dated Aug. 2006.
Haines et al., "Argon neutral plasma energy for laparoscopy and open surgery recommended power settings and applications", Royal Surrey County Hospital, Guildford Surrey, UK, dated Oct. 2009.
Marino, M.D., "A new option for patients facing liver resection surgery", Thomas Jefferson University Hospital, dated Mar. 24, 2005.
McClurken et al., 2001, "Collagen shrinkage and vessel sealing", TissueLink Medical, Inc., Dover, NH; Technical Brief #300.
McClurken et al., 2002, "Histologic characteristics of the TissueLink Floating Ball device coagulation on porcine liver", TissueLink Medical, Inc., Dover, NH; Pre-Clinical Study #204.
Plasma Surgery: A Patient Safety Solution (Study Guide 002), dated Feb. 25, 2010.
PLASMAJET Neutral Plasma Coagulator Brochure mpb 2100—K080197, dated Oct. 2006.
Premarket Notification 510(k) Submission, Plasma Surgical Ltd. CoagSafe™, Section 4 Device Description—K030819, dated Mar. 14, 2003.
Premarket Notification 510(k) Submission, Plasma Surgical Ltd. PlasmaJet®, Section 11 Device Description—K080197, dated Jan. 25, 2008.
Premarket Notification 510(k) Submission, Plasma Surgical Ltd. CoagSafe™, Section 5 Substantial Equivalence—K030819, dated Mar. 14, 2003.
Sonoda et al., "Pathologic analysis of ex-vivo plasma energy tumor destruction in patients with ovarian or peritoneal cancer", Gynecology Service, Department of Surgery—Memorial Sloan-Kettering Cancer Center, New York, NY—Poster, dated Feb. 5, 2009.
The Edge in Electrosurgery From Birtcher, 1991, Brochure—Appendix 4 of K030819.
The Valleylab FORCE GSU System, Brochure—Appendix 4 of K030819, dated Jan. 1991.
TREAT, "A new thermal device for sealing and dividing blood vessels", Dept. of Surgery, Columbia University, New York, NY, dated Jun. 29, 2005.
White Paper—A Tissue Study using the PlasmaJet for coagulation: A tissue study comparing the PlasmaJet with argon enhanced electrosurgery and fluid coupled electrosurgery, dated Oct. 23, 2007.
White Paper—Plasma Technology and its Clinical Application: An introduction to Plasma Surgery and the PlasmaJet—a new surgical technology, dated Oct. 23, 2007.
Proprierety device drawing submitted under MPEP 724, dated Mar. 14, 2003.
Proprierety device drawing submitted under MPEP 724, dated 2002.
Proprierety device drawing submitted under MPEP 724, dated Jan. 18, 2008.
Proprierety device drawing submitted under MPEP 724, dated 2002.
Proprierety device drawing submitted under MPEP 724, dated Feb. 26, 2003.
Severtsev et al., "Comparison of different equipment for final haemostasis of the wound surface of the liver following resection", Dept. of Surgery, Postgraduate and Research Centre, Medical Centre of the Directorate of Presidential Affairs of the Russian Federation, Moscow, Russia—K030819, dated Jun. 1997.
Video—Tumor Destruction Using Plasma Surgery, by Douglas A. Levine, M.D., dated Apr. 9, 2008.
Video—Laparoscopic Management of Pelvic Endometriosis, by Ceana Nezhat, M.D., dated Nov. 12, 2007.
Video—Tissue Coagulation, by Denis F. Branson, M.D., dated Dec. 4, 2008.
Office Action of U.S. Appl. No. 11/890,937, dated Apr. 3, 2013.
Notice of Allowance and Fees Due of U.S. Appl. No. 13/357,895, dated Feb. 21, 2013.
Chinese Office Action of Chinese application No. 200780100857.9, dated May 30, 2013.
Canadian Office Action of Canadian application No. 2,695,650, dated Jun. 18, 2013.
Canadian Office Action of Canadian application No. 2,695,902, dated Jun. 12, 2013.
Examiner's Answer to Applicant's Appeal Brief in U.S. Appl. No. 11/482,580, dated Jun. 18, 2013.
Office Action of U.S. Appl. No. 12/841,361, dated Jul. 31, 2013.

\* cited by examiner

FIG. 4A-D

METHODS OF SEALING VESSELS USING PLASMA

FIELD OF INVENTION

The present invention relates to methods for vessel sealing in living organisms using plasma.

BACKGROUND

The human body has various types of vessels for the exchange of fluids. Such vessels include bronchi, which carry air in lung tissue; bile ducts, which carry bile in liver tissue; lymph vessels, which carry lymph throughout the body; and blood vessels, which carry blood throughout the body. Denaturing of collagen present in vessel walls plays a major role in vessel sealing. Because all these types of vessels have a similar collagen structure in the walls, the processes involved in their sealing are similar. Blood vessels require sealing in virtually any surgery, and the following discussion, while applying to all above-mentioned vessels, is exemplified by sealing of human blood vessels.

There are several types of blood vessels, including arteries, veins, and capillaries. Arteries carry oxygen-rich blood away from the heart. As a result of heart contractions, arteries are under pressure typically varying from 80 mmHg to 120 mmHg. In contrast, veins carry oxygen deprived blood towards the heart and have a constant blood pressure which is typically below 10 mmHg. Capillaries are the small blood vessels through which the actual exchange of water and chemicals between blood and tissue occur. Their diameter is large enough to allow red blood cells to pass single file. In tissues, capillaries typically form dense networks referred to as capillary beds. Vessels of each type may also vary significantly in size and flow rate. Generally, however, the vessels of larger diameter have a higher flow rate.

During surgery, tissue dissection results in severing vessels that pass through the plane of dissection. It is desirable to seal the severed vessels quickly to prevent the escape of vital fluids and to reduce the risk of foreign matter entering into the vessel. Bleeding from severed blood vessels during surgery is one of the most well studied and often encountered situations requiring vessel sealing. Severing capillaries results in tissue bleeding. Severing of larger vessels may result in excessive bleeding, which obscures the surgical site, may require blood transfusions, and even threaten the patient's life. Therefore, the rapid coagulation of tissues and sealing of blood vessels is desirable. Similarly, the rapid sealing of lymph vessels, bronchi, and bile ducts when severing of those vessels occurs is also desirable.

Significant amounts of fibrous protein called collagen present in tissue and vessel walls make coagulation possible. Heat causes this collagen to denature, and as a result the collagen swells and becomes adhesive. For vessels, denaturing of collagen results in contraction of the vessel walls at the heated region. If heat is maintained, the vessel walls contract until the vessel is completely occluded and fluid flow stops. Various forms of energy can be used for generating heat to be applied to the vessel walls to achieve the sealing effect.

In the case of blood vessels, there are important differences between the process of blood vessel sealing as described above and tissue coagulation. Tissue coagulation involves applying energy to the tissue, without regard to the actual location of severed capillaries. Heating the tissue results in its swelling as well as the formation of a necrosis layer. This necrosis layer comprises a porous layer of desiccated cells called a spongy layer, and a gel-like compact layer formed from the denatured protein of the tissue cells and blood. The capillaries present in the tissue are small enough and have a low enough blood pressure to be effectively sealed by this process.

In contrast, larger blood vessels cannot be sealed through tissue coagulation alone, because the necrosis layer cannot hold the blood pressure of such vessels. Several types of devices known in the art may be used for sealing larger blood vessels. These devices are typically suited for the specific purpose of vessel sealing and during surgery have to be used in addition to other surgical devices.

One such device is the thermal tweezers, which incorporates a heating wire in one of two prongs and is disclosed for example in U.S. Patent Publication No. US 2006/0217706. A current passes through the wire and causes this prong to heat up. When the tweezers clamp down on a blood vessel, the heat simultaneously cuts the blood vessel and seals the two severed ends. The temperature near the wire is high enough to vaporize tissue, while the temperature further away from the wire is at a level suitable to denature the collagen in the blood vessel walls. This temperature distribution ensures that when the blood vessel is completely severed, both ends are sealed and blood no longer flows. Because of its specialized purpose, the thermal tweezers are not suitable for general tissue coagulation. Further, the device requires an exposed portion of a blood vessel onto which it can clamp. This means that the device cannot easily seal the end of a blood vessel severed during tissue dissection, where the severed end does not protrude beyond the dissection surface.

Another type of device is the electrocauterizer, which may be monopolar or bipolar. In a typical monopolar device, disclosed for example in U.S. Pat. No. 4,128,099, an active electrode is in close proximity to the treated region, such as the severed end of a blood vessel. The active electrode typically has a small surface for concentrating a relatively large amount of electrical energy. An inactive return electrode is affixed on the patient at a remote location. With this arrangement of electrodes, the electrical current passes from the active electrode to the treated region and then through the patient to the return electrode.

Among the drawbacks of a monopolar electrocautery devices is the unpredictable and uncontrollable nature of the electric current's pathway. The current may jump from one area of the surgical site to another, undesirably affecting the neighboring tissues. This, in turn, limits its utility as the device energy cannot be reliably directed to a single vessel desired to be sealed. Another drawback stems from the reliance of these devices on the electrical conductivity of liquids present at the surgical site or in a vessel to pass current. Some liquids carried in vessels, such as lymph, are nonconductive and a monopolar electrocautery device cannot be used for sealing of such vessels. Further, because the current passes through the patient's body, the current can adversely effect tissue beyond the surgical site. This essentially prohibits the use of such devices on tissues sensitive to electric currents, such as those of the heart or brain.

Bipolar electrocautery devices overcome some, but not all, of the limitations of monopolar devices. A typical bipolar device, such as the one disclosed for example in U.S. Pat. No. 7,118,570, has two electrodes in close proximity to each other, and, in operation, a current passes between them. This localizes the current to a small region, and only tissue in this region experiences the desired thermal changes. The two electrodes can be incorporated into tweezers that simultaneously apply mechanical force and thermal energy to the clamped vessel.

While more suitable for sealing vessels, a bipolar configuration also suffers drawbacks. Fundamentally, this device still applies current to the tissue, and therefore is still unsuitable for vessels carrying nonconductive liquids and tissues sensitive to electric currents. Additionally, because the vessel to be sealed has to be positioned between the two electrodes, the bipolar electrocautery devices suffer the same drawback as the thermal tweezers as it requires a part of the vessel to be exposed.

Another type of device used for sealing blood vessels is an ultrasonic device. This device utilizes an active jaw and an anvil surface for the other jaw. The active jaw uses a piezoelectric element to vibrate at ultrasonic frequencies. The vibrations caused in the tissue trapped between the two jaws create heat by internal friction. Drawbacks of this device are similar to the other devices in tweezer configurations, namely that an exposed portion of a blood vessel is required for clamping the vessel.

None of the presently known devices are capable of sealing vessels by using only heat, without electricity or mechanical force. Further, the prior devices are inconvenient for surgeons because they require a switch of devices in the middle of the procedure. For example, when a surgeon makes an incision with a scalpel, he will have to set the scalpel aside and use another device to seal vessels. This diverts the surgeon's attention and introduces another device into the surgery.

Presently, plasma devices are used for cutting, evaporating, and coagulating tissues. As such, these plasma devices can be used for sealing smaller vessels in tissue. One example is the device disclosed in U.S. Pat. No. 5,843,079. But while plasma devices are used for cutting, evaporation, and coagulation of tissues and smaller vessels under 1 mm in diameter, such devices could not be used successfully for sealing larger vessels. Because plasma devices are already used for a variety of surgery-related functions it is desirable to enable these devices to seal vessels safely and effectively.

SUMMARY

A method of sealing an opening end of a liquid-carrying vessel of at least 1 mm in diameter in a living organism is disclosed. The method comprises: directing a plasma flow into an opening end of the liquid-carrying vessel; evaporating a liquid from a portion of the liquid-carrying vessel with the plasma flow, wherein the portion extends from the opening end of the liquid-carrying vessel to a depth equal to at least the liquid-carrying vessel diameter; contracting the walls of the liquid-carrying vessel in the portion of the liquid-carrying vessel from which the liquid is evaporated by heating the walls; and forming a seal from the contracted walls of the liquid-carrying vessel.

When discharged from the plasma-generating device, the generated plasma flow has the initial temperature of at least 11 kK and the diameter of at least 0.45 mm. The trajectory of the plasma flow is preferably at an angle of less than 20° to an axis of the liquid-carrying vessel at the opening end. Optimally, the trajectory of the plasma flow is substantially aligned with the axis of the liquid-carrying vessel at the opening end. The generated plasma flow has a substantially parabolic temperature distribution.

Contracting the vessel walls and ultimately sealing the vessel is accomplished as a result of denaturing collagen in the walls of the liquid-carrying vessel. The liquid-carrying vessel may be a blood vessel, a bile duct, or a lymph vessel.

For gas-carrying vessels, such as bronchi, the method of sealing is different because there is no liquid in the vessel to evaporate. For those vessels, the method comprises directing a plasma flow into an opening end of the fluid-carrying vessel; contracting walls of the fluid-carrying vessel; and forming a seal from the contracted walls of the fluid-carrying vessel.

To accomplish the sealing, the operator performs a method that comprises discharging a plasma flow using a flow of a plasma-generating gas with a flow rate of 0.2-0.5 L/min at room temperature, when discharged, the plasma flow having a diameter of at least 0.45 mm, and an initial discharge temperature of at least 11 kK; and directing the plasma flow into an opening of a vessel having a diameter of at least 1 mm in a living organism. The plasma-generating device is held at a distance of 10-30 mm from the opening of the blood vessel. If after holding the device for at least 0.5 s in that position, the blood flow from the vessel opening is not eliminated, the distance is decreased. Once the blood flow is eliminated, the device is held at that position for 1-2 s. The plasma is directed into the opening of the blood vessel preferably at an angle of at most 20° to the axis of the blood vessel at the opening. For vessels with the diameter of 3 mm, if no seal is formed after approximately 2 s after the blood flow is eliminated, the plasma flow may be directed to different points around the vessel in a circular fashion. Heating the tissue surrounding the opening of the vessel may facilitate the vessel sealing.

DESCRIPTION OF THE PREFERRED EMBODIMENTS

For the purposes of this disclosure, the term "vessel" and its variations refers to fluid transporting structures in the body. The method for sealing vessels using plasma may be used for sealing vessels such as blood vessels, bronchi, bile ducts, or lymph vessels of a living organism such as a human or other animal. The following discussion uses the sealing of human blood vessels as an example. However, embodiments of the method are effective for other types of human vessels and also for animal vessels. To the extent there are any differences between the embodiment of the method as it us used to seal other types of vessels, such differences are disclosed.

Figure 1:
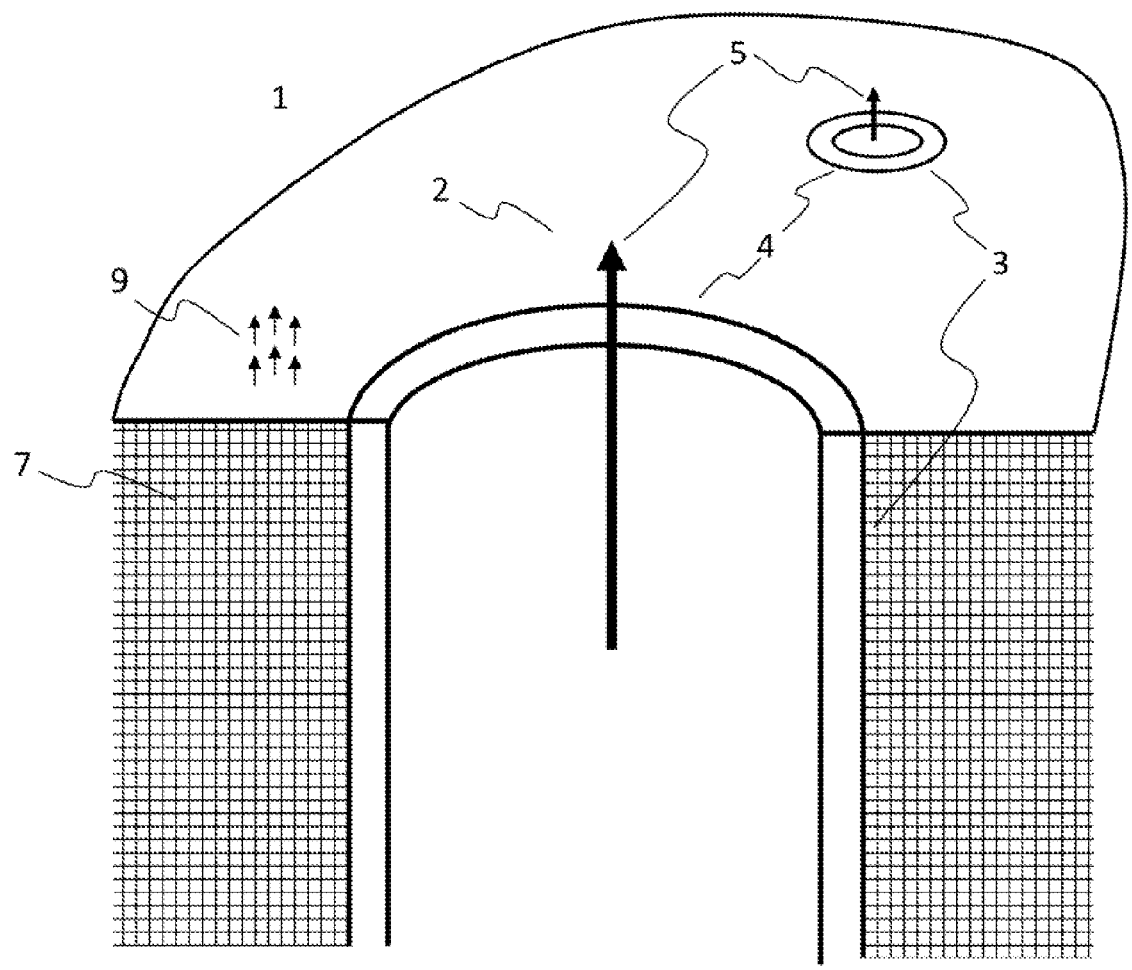
FIG. 1 illustrates a surgical site created by the dissection of tissue during surgery.

Referring to FIG. 1, surgical site 1 is created by the dissection of tissue during surgery. Blood vessels 3 are severed along plane of dissection 2, and have opening ends 4, from which blood flows. Blood flows 5 continue at a substantially constant rate until the blood vessels are sealed. Blood vessels 3 are either arteries or veins, and the sizes and blood flow rates of these vessels can vary. Typically, blood flow is measured in mL/min or L/min. However, in the context of a single blood vessel, the blood flow rate can be expressed in mm/s. In other words, the blood flow rate in a blood vessel can be measured by how far a particle of blood travels in a unit of time.

Capillary bed 7 makes up another component of the vascular system present at surgical site 1. The capillaries that comprise capillary bed 7 are also severed along plane of dissection 2. Tissue blood flow 9 is produced from capillary bed 7 and contributes to the total bleeding at surgical site 1 after dissection.

Embodiments of the vessel sealing method have been experimentally determined to be effective for all types of fluid-carrying vessels, for diameters up to 4 mm and for flow rates of the respective liquid (such as blood, lymph, or bile) up to 4 min/s. Embodiments of the methods are likewise effective for sealing of gas-carrying vessels, such as the bronchi in lung tissue with a diameter of up to 4 mm. In some embodiments of the vessel-sealing method the coagulation of tissue, i.e., stopping tissue bleeding flow 9, may be accomplished as well.

Figure 2A:
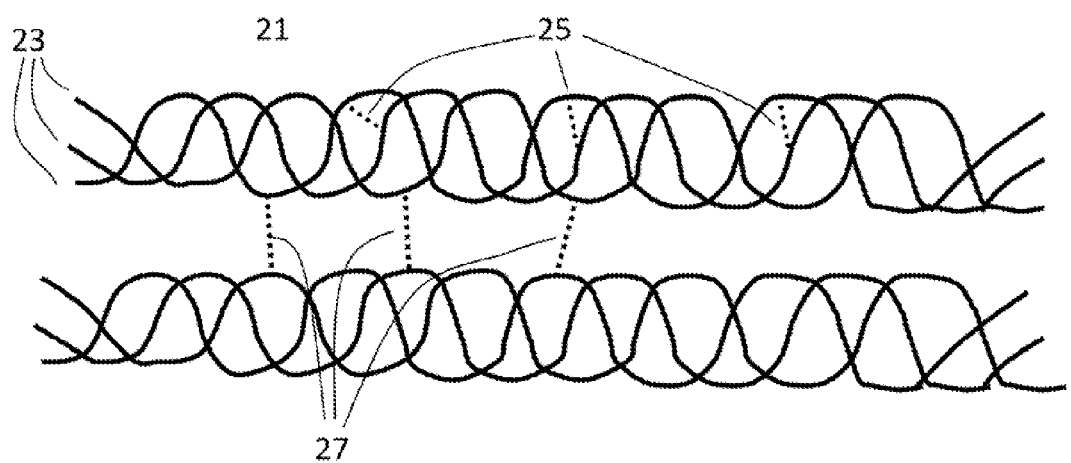
FIG. 2A illustrates the micro-structure of collagen fibers.
Figure 3:
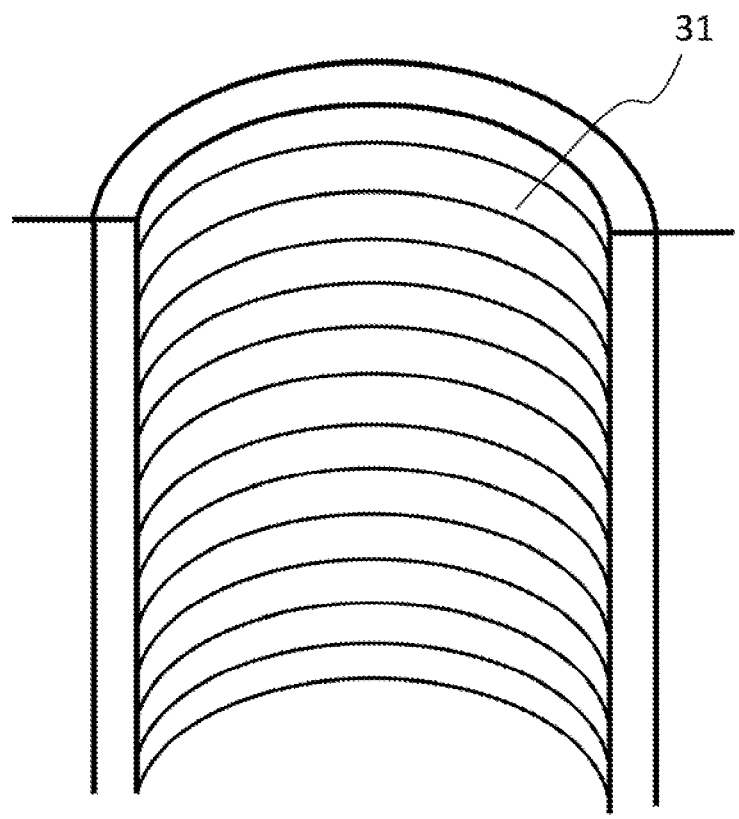
FIG. 3 illustrates the structure of collagen fibers in the walls of a blood vessel.

Turning now to the biology of vessel sealing, the presence and structure of collagen in vessel walls allows for the entirely thermal process of sealing to occur. Referring to FIG. 2A, collagen 21 is a connective tissue composed of three polypeptide chains 23 in a triple helix formation. These triple helix molecules combine with others to form more complex structures. Vessel walls contain a significant amount of fibrous collagen, which consists of many triple helices arranged in a parallel, quarter-staggered end overlap pattern, as shown in FIG. 2A. The triple helices are held together internally by intramolecular hydrogen bonds 25, and intermolecular crosslinks 27 connect the separate helices to each other. In vessels, these fibers 31 are arranged annularly throughout the walls, as shown in FIG. 3.

Figure 2B:
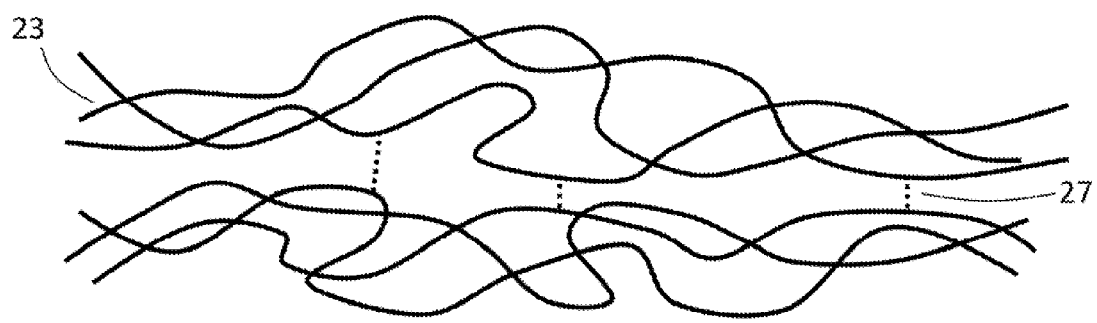
FIG. 2B illustrates the structure of collagen fibers after denaturing.

When heated, the collagen in the vessel walls undergoes an irreversible reaction, called denaturation. Referring to FIG. 2B, when heated the triple helix structure collapses as the intramolecular hydrogen bonds break. This causes the polypeptide chains 23 to uncouple and the entire helix to unzip. As this occurs, only the intermolecular crosslinks 27 remain and the peptide chains take on a more random structure. As a result, the collagen structure shrinks along the dimension in which it was aligned while simultaneously expanding in the other directions. Additionally, the exposure of hydrogen bonding groups along the peptide chains makes forming new bonds between adjacent chains possible. As a result, the collagen becomes adhesive and forms a tangled intertwined matrix of protein strands.

The swelling that occurs when the collagen in vessel walls denatures can completely seal the vessel. Because collagen fibers 31 are arranged annularly throughout the walls of the vessel as shown in FIG. 3, this swelling is substantially perpendicular to the axis of the vessel. The surrounding tissue constrains the outward expansion of the vessel walls, facilitating the swelling of the vessel walls inward.

Collagen also exists throughout the tissue surrounding vessels 3, which will also cause swelling as heat is transferred through to the tissue. This heat can be transferred directly by a plasma flow or by heat diffusion through the vessel walls of a vessel being sealed. As heat is transferred to the adjacent tissue, the collagen in that tissue denatures and "pushes" the blood vessel walls further inwards. This extra source of swelling in the surrounding tissue contributes to the contraction of the vessel walls.

In this disclosure, the term "contract" and its variations refer to this inward swelling. Contraction may be accomplished by heating and denaturing collagen in the vessel walls and by heating surrounding tissue, which causes further inward movement of the vessel walls. In embodiments of the method, contraction ultimately leads to vessel sealing, also referred to as occlusion.

As a general overview of the preferred embodiment, sealing occurs during surgery. To coagulate tissue and seal vessels, a plasma surgical device with a plasma output channel of 0.8 mm in diameter is used in a coagulation mode. When discharged, the plasma flow in this mode has a temperature preferably 12.5-15.5 kK. The flow rate of the plasma-generating gas at room temperature is preferably 0.25-0.5 L/min. These preferred ranges apply to all liquid-carrying vessels. For gas-carrying vessels, however, the preferred temperature range is the same but the flow rate of the plasma is preferably between about 0.12-0.37 L/min. The underlying physical processes and considerations leading to these preferable ranges are disclosed at length in the following discussion. First, however, it is beneficial to discuss how this plasma flow is used by an operator to achieve vessel sealing during surgery.

Figure 10A:
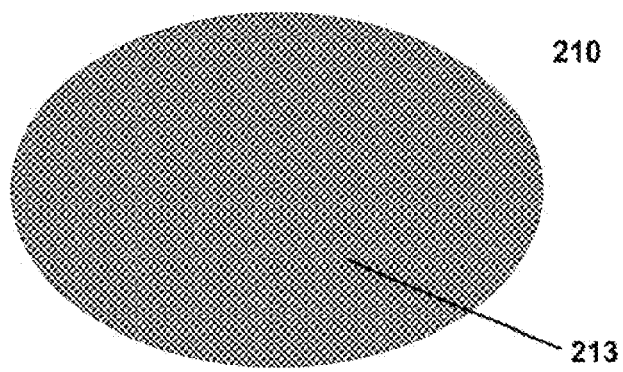
FIGS. 10A-E illustrate a procedure of blood vessel sealing disclosed herein.
Figure 10B:
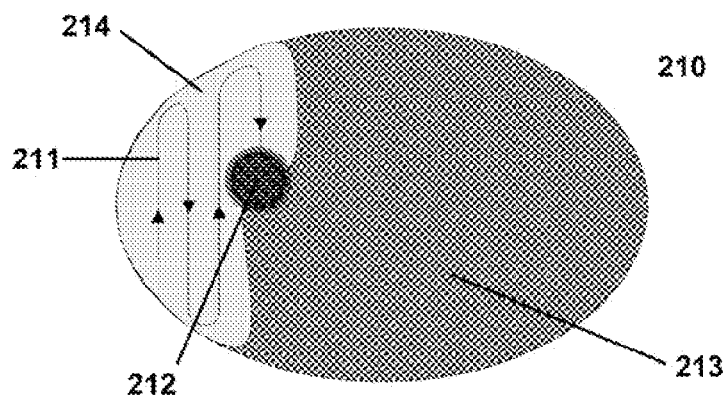

When performing dissection of a tissue, for example a liver, the surgical site quickly becomes covered with blood resulting from tissue and vessel bleeding. FIG. 10A schematically shows surgical site 210 covered with blood 213. Stopping the bleeding quickly allows the operator to resume the surgery. To stop the bleeding, the operator holds the end of the plasma generating device at a distance of 10-30 mm, preferably around 15-25 mm, from the tissue. At this distance, the operator "sweeps" the plasma flow over the tissue accomplishing tissue coagulation. The operator begins to "sweep" the site with the plasma flow along an exemplary path 211 as shown in FIG. 10B. As the tissue of the area of dissection is coagulated 214, the fluid covering it dries up or evaporates and the operator detects dissected vessels, the sealing of which is the main focus of this disclosure. When the operator comes across a vessel, he observes a depression 212 in the dissected surface as shown in FIG. 10C.

Figure 10C:
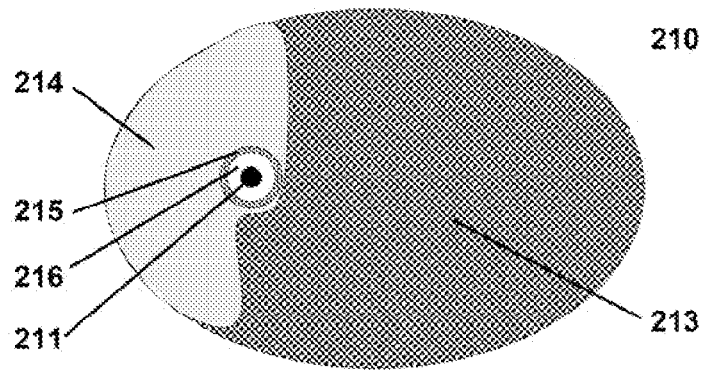

By aiming the device toward the depression for approximately 0.1-0.2 s, the operator removes blood covering it as shown in FIG. 10C. By continuing to aim the device towards the vessel, the operator directs the plasma flow 211 inside the vessel. After approximately 0.2-0.5 s of directing the flow inside the vessel, the operator observes empty volume 216 surrounded by vessel walls 215. If the vessel is a liquid-carrying vessel, such as a blood vessel, the operator may not observe empty volume 216. This indicates that the liquid flow rate in this vessel is relatively high and the rate of evaporation of the liquid with plasma is lower than the liquid flow rate. In this case, the operator moves the plasma generating device closer to the tissue while directing the plasma into the vessel for another period of approximately 0.2-0.5 s to create empty volume 216. Moving the device closer to the vessel may be repeated until empty volume 216 is observed. It should be understood that instead of incremental moves, the operator may elect to move the plasma-generating device closer to the tissue in a continuous motion, until empty volume 216 is observed.

Once empty volume 216 is observed, the operator continues to direct the plasma flow inside the vessel from that distance, which results in vessel contraction. For vessels of diameter less than 3 mm, contraction takes approximately 1-1.5 s. For vessels of diameter greater than 3 mm, contraction takes approximately 1.5-2 s.

Figure 10D:
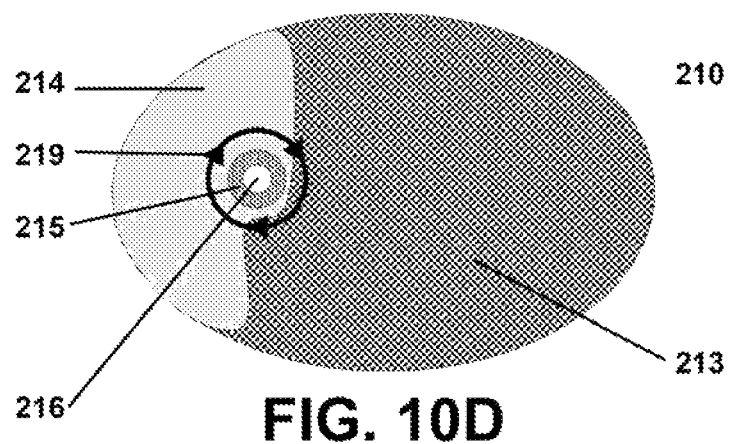
Figure 10E:
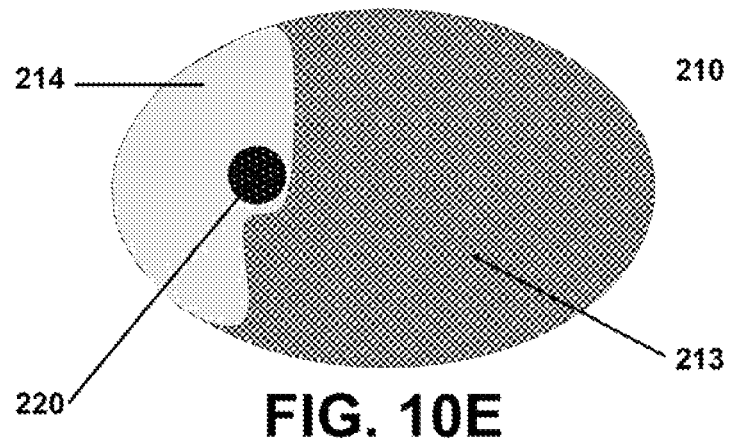

Contraction may not completely occlude the vessel, particularly if the diameter of the vessel is relatively large i.e., greater than 3 mm. In this case, as shown in FIG. 10D, the operator "sweeps" the tissue surrounding the contracted vessel with the plasma flow in a circular motion 219. If the fluid flow rate was high enough to require moving the plasma generating device relatively close to the tissue while directing the plasma flow into the vessel, the operator may move the device back for circular "sweeping" 219. By "sweeping" the tissue surrounding the contracted vessel in a circular fashion, the operator causes tissue adjacent to the vessel to further heat. As a result the collagen in the surrounding tissue swells and "pushes" the vessel wall inward to further contract and completely occlude. When the vessel is completely occluded, vessel walls 215 form a robust seal 220, as shown in FIG. 10E. Typically for vessels with the diameter of less than 3 mm, circular sweeping shown in FIG. 10D is not required to achieve the robust seal shown in FIG. 10E. For those vessels directing the plasma flow into the vessel for approximately 1-1.5 s is sufficient for sealing the vessel.

Figure 4A:
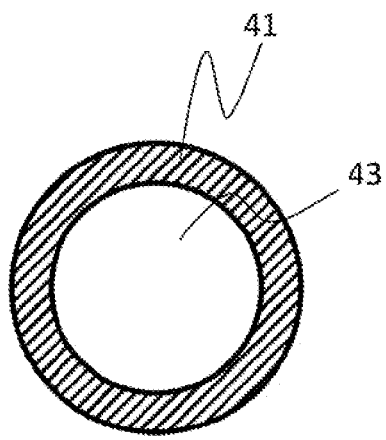
FIG. 4A-D illustrate various stages of the contraction of the walls of a blood vessel.
Figure 4B:
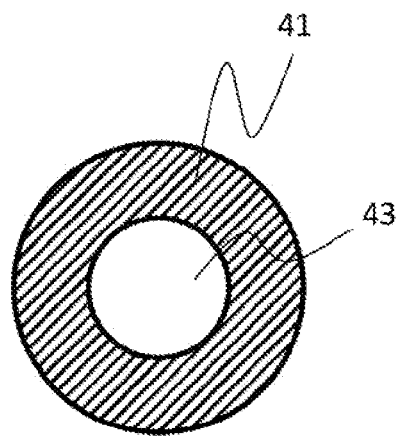
Figure 4C:
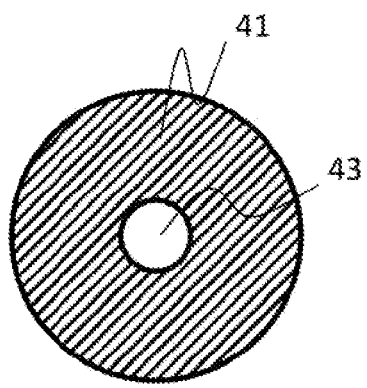
Figure 4D:
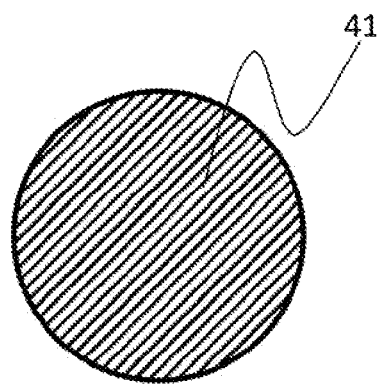

FIGS. 4A-4D schematically show a progression of the sealing process, depicting the vessel walls 41 and the vessel opening 43. FIG. 4A shows the vessel before heat is applied. FIGS. 4B and 4C show intermediary states where the collagen has begun to denature and to cause the vessel walls to contract. When sufficient heat is applied, collagen strands that were originally separate come into contact. Intermolecular bonds that form between these strands of denatured collagen ensure that the vessel walls adhere permanently. FIG. 4D shows this complete occlusion of the vessel opening. The resulting seal, if sufficiently thick, completely prevents further bleeding or other fluid flow from the vessel. Notably, mechanical force, applied for ensuring vessel walls contact to facilitate the 'welding' process as was done in prior art, is not necessary for this sealing to occur.

In the preferred embodiment, for blood vessels of up to 4 mm in diameter, sealing is accomplished by directing a plasma flow into opening end 4. The plasma flow must be able to penetrate into blood vessel 3 to a depth of 1-1.5 times the diameter of the vessel. Penetration of the plasma flow deeper than 1.5 times the diameter does not occur because the plasma flow is cooled significantly by the vessel walls and loses its penetration ability past this depth. Penetration of the plasma flow involves gradually evaporating the blood inside of the vessel to the desired depth and then maintaining that depth by evaporating blood as it flows into the portion of the vessel free of blood. By doing this, the plasma flow heats a significant surface area of the blood vessel walls from inside the vessel and transfers heat to the adjacent tissue.

The preferred embodiment adapted for gas-carrying vessels, such as bronchi, does not involve evaporating fluids native to the vessel. The bronchi will not be obscured by fluids after dissection, and so in the preferred method the operator does not perform the steps of uncovering the bronchi or evaporating an opposing fluid flow inside the bronchi. The plasma flow in this embodiment penetrates to the depth of 1-1.5 times the diameter of the vessel and accomplishes sealing by heating a significant surface area of the vessel wall from inside the vessel.

Figure 7:
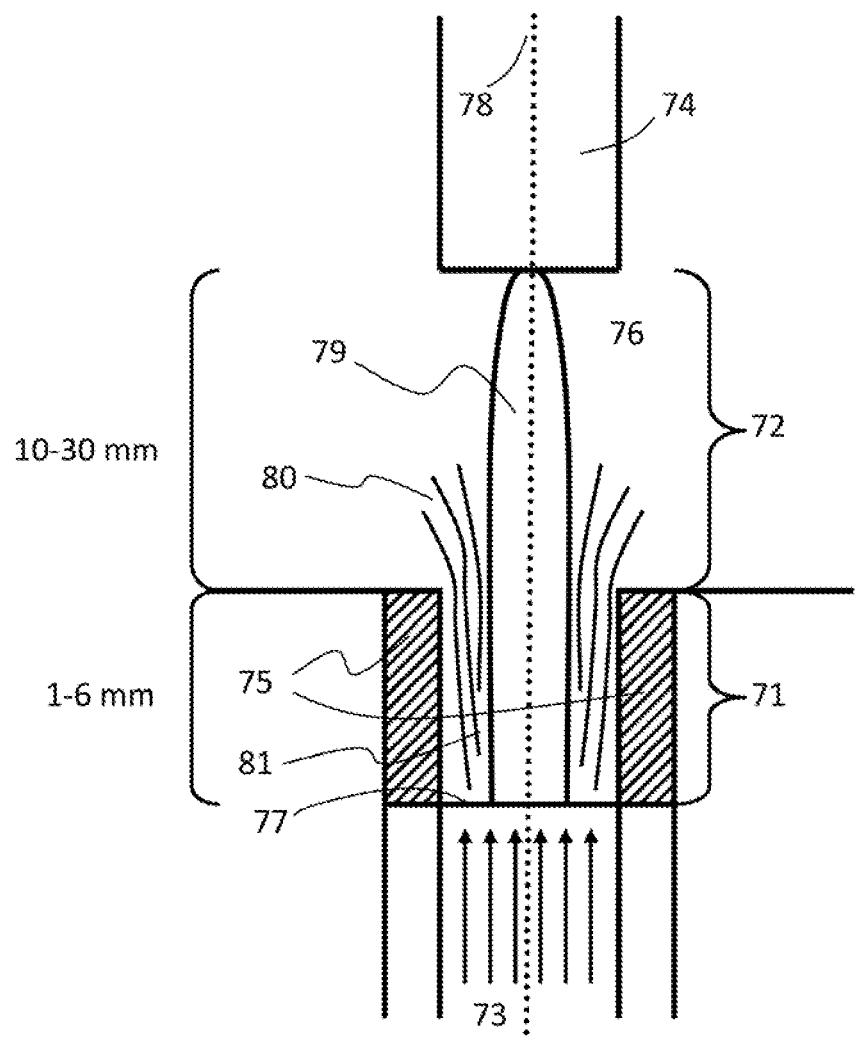
FIG. 7 illustrates a sectional view of a blood vessel with a plasma flow penetrating significantly into the vessel.

Referring to FIG. 7, in terms of biological processes, as plasma flow 79 enters the vessel it evaporates fluid from portion 81 of the vessel and simultaneously heats walls 75 of the vessel to denature collagen in that portion. As a result, the collagen swells into the volume freed up from fluid evaporated by plasma 79. After plasma is directed into the vessel in such a way for preferably 1-2 s, the vessel is sealed completely.

Figure 6:
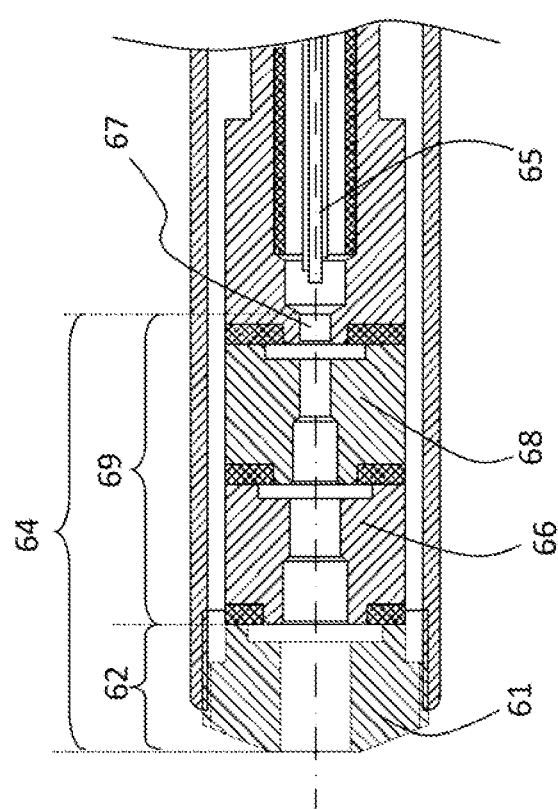
FIG. 6 illustrates a sectional view of a plasma generating device.

An example of a device that can produce a plasma flow suitable for the above method(s) is described in U.S. Pat. No. 7,589,473, incorporated herein by reference for all purposes. Although the U.S. Pat. No. 7,589,473 describes generating pulsed plasma, the device disclosed therein may be used for generation of continuous or modulated plasma flows suitable for vessel sealing. Briefly, FIG. 6 shows a suitable multi-electrode device that comprises anode 61, a cathode assembly 63, and a gas supply channel 65 for supplying a plasma generating gas, which is preferably argon. Plasma channel 64 is formed by anode 61 and two or more intermediate electrodes 66, 68.

The plasma channel 64 comprises heating portion 67, expansion portion 69, and anode portion 62. In expansion portion 69, the diameter of plasma channel 64 increases in a stepwise fashion toward the anode portion 62, and is preferably implemented in a number of sections. Heating portion 67 can be thought of as the first section, and anode portion 62 can be though of as the last section of the expansion. It has been determined that an increase in diameter of 0.4-0.6 mm is preferred. It was further determined that the length of each section is preferably greater than its diameter and less than two times its diameter. The diameter of anode portion 62 is determined by the desired application, such as vessel sealing. Accordingly, the diameter of the anode portion and the diameter of the heating portion dictate the internal geometry of the device. Variations are possible if the number of sections in expansion portion 69 is relatively large, but these variations would be operable as long as the relationships set forth above are observed.

In the preferred embodiment, the diameter of the anode portion is 0.75-0.85 mm, preferably 0.8 mm. This embodiment is adopted for tissue coagulation and vessel sealing. In another embodiment specifically adopted for tissue dissection coupled with vessel sealing, the diameter of anode portion 62 is 0.45-0.55 mm. In yet another embodiment, specifically adopted for tissue coagulation and blood vessel sealing, the diameter of the anode portion 62 is 1.15-1.25 mm. For convenience, the three embodiments are referred to as the 0.8 mm device, 0.5 mm device, and 1.2 mm device, respectively. In all embodiments, the diameter of the heating portion is 0.2-0.5 mm, preferably 0.4 mm. Unless otherwise specifically noted, the discussion refers to the embodiment having an anode portion 62 with diameter of 0.8 mm.

During operation, the plasma generating gas is supplied into plasma channel 64 through one or more gas supply passages 65 along cathode assembly 63. The plasma-generating gas is preferably argon, but another gas can also be used. A plasma flow is generated by heating the plasma generating gas as it passes through a plasma channel 64 by an electric arc established between cathode assembly 63 and anode 61. As the plasma traverses plasma channel 64, it expands from the diameter of heating portion 67 to the diameter of anode portion 62. The expansion occurs gradually to conform to the diameter of each section of expansion portion 69 that the plasma traverses. As the plasma exits the device through the outlet of plasma channel 64 in the anode portion 62, it has the desired diameter.

Heating of the plasma flow is non-uniform within plasma channel 64. The core plasma in the flow closest to the electric arc has the highest temperature. Plasma along the periphery of plasma channel 64 is distanced from the electric arc and is also cooled by the walls of the channel. As a result, the periphery plasma is significantly cooler than the core plasma. As the plasma transverses the plasma channel it acquires a substantially parabolic temperature profile, with a peak temperature at the center of the cross section. The plasma flow retains this substantially parabolic temperature profile after exiting anode portion 62 and as it propagates away from the device towards the surgical site.

A plasma flow with a substantially parabolic temperature distribution does not have a single temperature. For many purposes, however, it is useful to characterize the plasma flow with a single representative temperature. One way to characterize the temperature of the plasma flow is to consider the temperature in the core of the flow. Another way to characterize the temperature of the plasma flow is to consider the average temperature in the flow at a given cross section. Embodiments of the device used for vessel sealing maintain an electric arc during operation. The current in the electric arc governs the temperature of core plasma at anode portion 62. It has been found that the representative temperature of the plasma flow discharged from the device is approximately 1,000 K less than the core plasma temperature at anode portion 62. The term "initial temperature" and its variations refer to a representative temperature, preferably the core temperature, of the plasma flow as it is discharged from the plasma-generating device. Unless otherwise specifically noted, any mention of plasma flow temperature in this disclosure refers to a representative temperature, which is a temperature of a substantial portion of the plasma flow as it is discharged.

Turning back to the operation of the device, the maximum current the device can use in the continuous mode is approximately 12 A. Passing a continuous current higher than 12 A may result in melting of the device elements. It is therefore preferable to operate the device with a current that is 12 A or below. Another limitation on the operational parameters of the device is the power of the plasma flow as it reaches the surgical site. FDA approves devices for coagulation that operate in the range of 10-120 W. The optimal range for sealing vessels was found to be 20-60 W, but may be higher.

In the preferred embodiment, the plasma-generating device generates a continuous plasma flow. In other embodiments, the device may generate modulated or pulsed plasma flow. Modulated plasma flow is a flow in which the current is periodically increased to achieve a higher power during those increases; pulsed plasma refers to a flow in which the current is periodically ceased or reduced to zero. Experiments show that some vessels, such as bronchi, may only be sealed with continuous plasma flow, while sealing of other vessel types may be performed by either continuous, modulated, or pulsed plasma.

The fundamental condition for blood vessel sealing is the ability of the plasma flow to penetrate into the blood vessel to the depth of 1-1.5 times the diameter of the vessel and at that depth to evaporate the incoming blood. This is illustrated in FIG. 7 that shows a blood vessel being sealed. The path of the plasma flow is from the tip of the device 74 to the incoming blood flow edge 77 where incoming blood evaporates. This path comprises distance traversed through the air 72 and distance traversed inside the vessel 71. The fundamental condition of vessel sealing results in very specific plasma flow characteristics. First, the plasma flow has to be able to traverse 10-30 mm of air and penetrate into the vessel to the required depth. Second, at that depth (1-1.5 times the diameter), the plasma flow has to retain enough energy to heat the collagen in the vessel walls and to evaporate the incoming blood. For other liquid-carrying vessels, the plasma characteristics are approximately the same as for blood vessels.

For gas-carrying vessels, with no liquid evaporation during sealing, a lower plasma flow rate is effective.

The following discussion presumes the use of argon as the plasma-generating gas. Table 1 presents key properties of argon for different temperatures.

TABLE 1

| Temperature, T [K] | Density, $\rho$ [kg/m$^3$] | Enthalpy, h [MJ/kg] |
|---|---|---|
| 290 | 1.6794 | 0.150 |
| 500 | 0.9740 | 0.241 |
| 1,000 | 0.4870 | 0.501 |
| 2,000 | 0.2440 | 1.021 |
| 2,500 | 0.1950 | 1.281 |
| 3,000 | 0.1623 | 1.541 |
| 4,000 | 0.1218 | 2.061 |
| 4,500 | 0.1084 | 2.321 |
| 5,000 | 0.0974 | 2.581 |
| 5,500 | 0.0886 | 2.841 |
| 6,000 | 0.0814 | 3.102 |
| 7,000 | 0.0699 | 3.636 |
| 8,000 | 0.0608 | 4.218 |
| 9,000 | 0.0532 | 4.976 |
| 10,000 | 0.0474 | 6.183 |
| 10,500 | 0.0448 | 7.122 |
| 11,000 | 0.0420 | 8.422 |
| 11,500 | 0.0394 | 10.124 |
| 12,000 | 0.0366 | 12.312 |
| 12,500 | 0.0336 | 15.016 |
| 13,000 | 0.0308 | 18.293 |
| 14,000 | 0.0252 | 26.513 |
| 14,500 | 0.0229 | 31.220 |
| 15,000 | 0.0208 | 35.845 |
| 15,500 | 0.0191 | 40.194 |
| 16,000 | 0.0178 | 43.911 |
| 17,000 | 0.0158 | 49.626 |
| 18,000 | 0.0144 | 53.456 |
| 19,000 | 0.0132 | 56.356 |
| 20,000 | 0.0121 | 59.284 |

For a plasma flow, the ability to traverse a distance in the air and then to penetrate into the vessel to a given depth depends on dynamic pressure, also called impact pressure, of the plasma flow. Dynamic pressure is closely related to the kinetic energy of fluid molecules. The equation for dynamic pressure can be expressed as:

$$P_d = \frac{g^2}{2\rho(T)},$$

where $P_d$ is the dynamic pressure in kg/(m*s$^2$), g is the flow density in kg/(s*m$^2$), and $\rho(T)$ is the plasma density in kg/m$^3$. The above equation shows that the dynamic pressure of the plasma flow can be increased by (1) increasing flow density (number of molecules passing through a unit of area per second) or (2) increasing the temperature, which decreases the plasma density.

Generating a plasma flow with a large dynamic pressure at the output of the device is not enough to ensure sufficient penetration of the plasma flow into the vessel. The penetration ability of a plasma flow actually depends on how rapidly the dynamic pressure decreases as the plasma flow propagates through the air to the surgical site and inside the vessel to be sealed. In this disclosure, the rate of the dynamic pressure decrease is referred to as the gradient of the dynamic pressure. If the dynamic pressure decreases rapidly after exiting the device the gradient of the dynamic pressure is large and significant penetration of the plasma flow into the vessel is difficult to achieve.

Figure 8B:
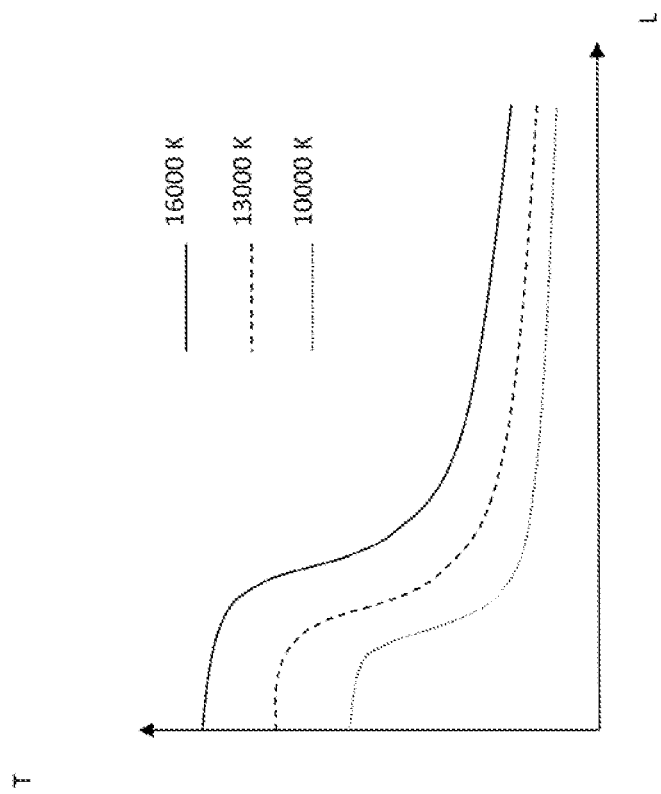
FIGS. 8A and 8B illustrate temperature profiles of laminar and turbulent flows along the plasma flow axis.
Figure 8A:
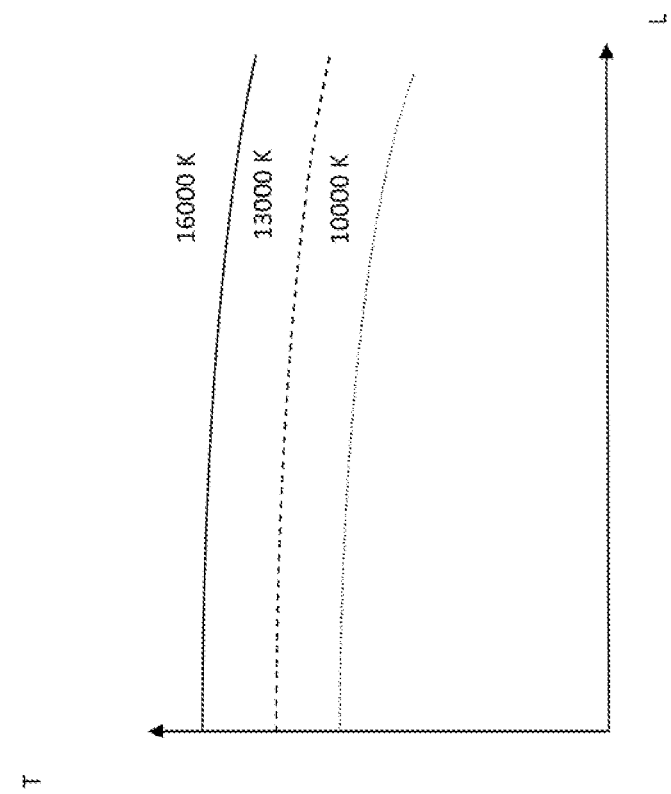

By their nature laminar flows maintain temperature and dynamic pressure, while turbulent flows do not. FIGS. 8A and 8B depict the temperature distributions along the plasma flow axis for laminar and turbulent flows, respectively. For laminar flows, shown in FIG. 8A, the temperature decreases slowly, while for turbulent flows, shown in FIG. 8B, the temperature drop sharply close to the outlet of the plasma channel. FIGS. 8A and 8B show that that laminar flows have a significantly smaller dynamic pressure gradient and a better penetration ability.

Laminar flow occurs when the viscous forces of a fluid are comparable to inertial forces. Laminar flow is characterized by the fluid flowing in lamina with no exchange of fluid between the neighboring lamina. The flow illustrated in FIG. 7, which maintains a narrow cross-sectional profile as it propagates away from tip 74 of the device, is an example of laminar flow. The temperate profile characteristic of a laminar flow such as the one seen in FIG. 8A implies that the dynamic pressure gradient is low and therefore the penetration ability of the flow is high.

Figure 9:
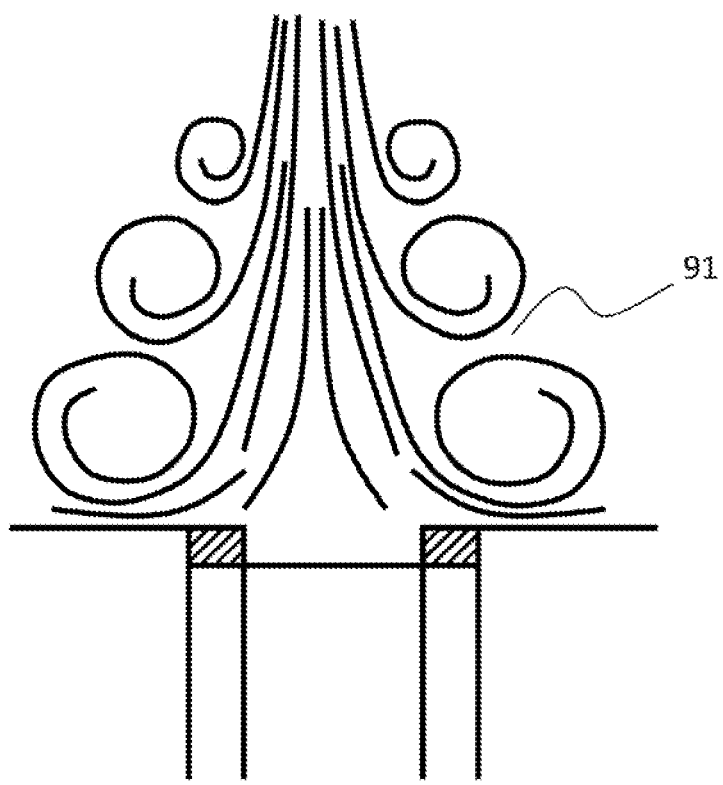
FIG. 9 illustrates the effect of turbulence preventing significant penetration of a plasma flow into a blood vessel.

Turbulent flow occurs when the inertial forces of plasma predominate viscous forces. A turbulent flow is characterized by rapid chaotic variation of pressure and velocity in space and time. As seen in FIG. 9, when the plasma flow 91 is turbulent the plasma flow mixes with the surrounding air. This mixing process gives rise to the rapid drop in temperature as the plasma flow propagates. The penetration ability of a turbulent flow, consequently, is also low because the gradient of the dynamic pressure in a turbulent flow is large.

In fluid mechanics, the Reynolds number of a fluid indicates if a given flow is laminar or turbulent. The Reynolds number is a dimensionless ratio of the inertial forces and viscous forces of the fluid flow. It takes into account factors such as the fluid velocity, viscosity, density, flow rate, and the geometry of the environment. The Reynolds number can be calculated analytically for a few simple geometries. For example, the equation for a fluid flowing through a pipe, which is an acceptable approximation of vessel sealing processes described herein, is as follows:

$$Re = \frac{4\rho Q}{\mu \pi d},$$

Where $\rho$ is the density of the fluid in kg/m$^3$, Q is the volumetric flow rate in m$^3$/s, $\mu$ is the dynamic viscosity of the fluid (Pa·s or N·s/m$^2$ or kg/m·s), and d is the pipe diameter (m). Laminar flows occur for Reynolds numbers less than a critical Reynolds number denoted by $Re^*_L$, which is an experimentally determined constant. If Reynolds number is above $Re^*_L$, the flow is turbulent. Because of its dependence on several temperature-related properties of the plasma flow, the Reynolds number is strongly influenced by temperature.

Not all laminar flows are suitable for vessel sealing. For example, a laminar plasma flow with a very low flow rate would not generate sufficient power for vessel sealing. The plasma flow rate can be measured in different ways. For convenience, operators and manufacturers of plasma-generating devices typically measure the flow rate in terms of the room-temperature plasma-generating gas flow rate in L/min. This provides a measure of the volume of room-temperature argon entering the plasma generating device. As shown in Table 1 above, the density of argon changes with temperature. Thus the room-temperature argon volume supplied to the device in a unit of time is significantly smaller than the volume of heated argon plasma exiting the device in that unit of time. To find this larger volumetric flow rate of the plasma flow, which is required for calculations of the Reynolds number, the flow rate is first converted into the mass flow rate, which is measured in kg/s and is temperature independent. The mass flow rate can then be turned back into a volumetric flow rate using the density of the heated plasma and used in the above equation for the Reynolds number.

The following example illustrates the increase in the volumetric flow rate when room-temperature argon is turned into 12.5 kK plasma. Assuming a room-temperature argon flow rate of 0.35 L/min, the volumetric flow rate expressed in m$^3$/s is $5.8 \times 10^{-5}$ m$^3$/s. Using the density of room-temperature argon gas, which is 1.6794 kg/m$^3$, the mass flow rate is calculated to be $9.8 \times 10^{-6}$ kg/s. When the mass flow rate is then turned back into a volumetric flow rate using the density of the hot plasma, which is approximately 0.0336 kg/m$^3$, the volumetric flow rate is $2.92 \times 10^{-4}$ m$^3$/s, or 17.5 L/min. The volumetric flow rate is higher for plasma with higher temperature, and it is this high-temperature flow rate that is used in computing the Reynolds number in the above equation.

Figure 11:
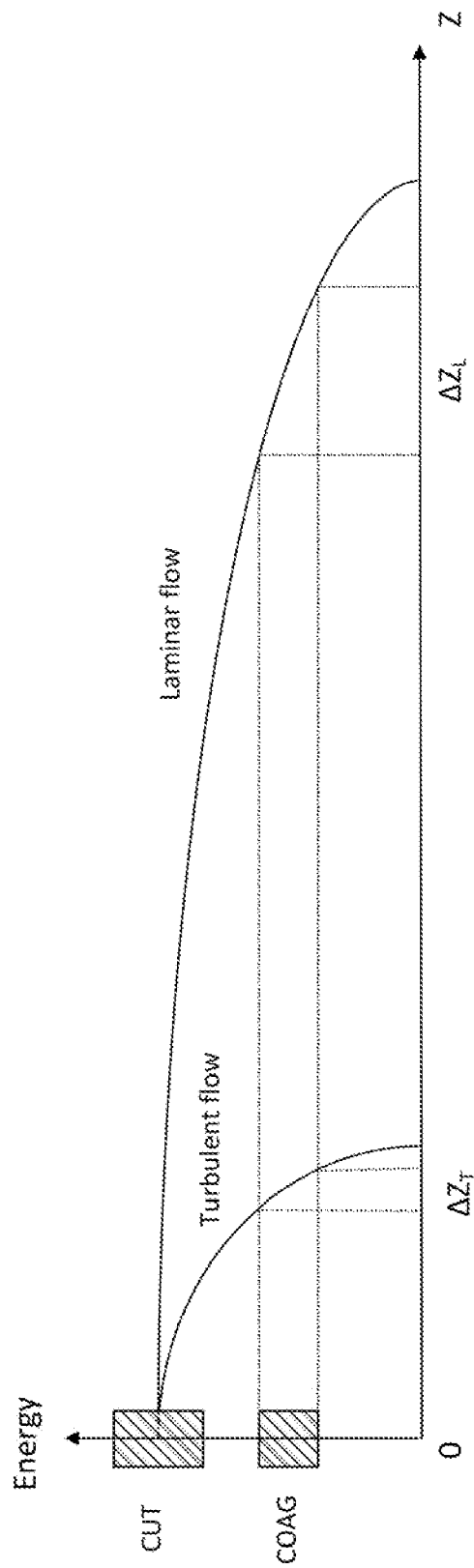
FIG. 11 illustrates distance ranges of turbulent and laminar flows for coagulation and vaporization.

Experiments confirm that only a laminar flow, such as the one in FIG. 8A, can traverse 10-30 mm of the air and then penetrate the vessel to a certain depth. A turbulent flow, as shown in FIG. 8B, would experience a significant temperature decrease close to the device and by the time such a turbulent flow reached the vessel, it would not have enough dynamic pressure for penetration. FIG. 11 illustrates the distance ranges for tissue coagulation and vessel sealing at which the plasma flow contains enough energy to deliver appropriate power to the surgical site. As seen from FIG. 11, a turbulent flow can only achieve these energy levels when the device is close to the tissue. This distance range for coagulation is very small, which makes the surgical procedure very difficult to perform. Even if the device is maintained in the desired distance range, turbulent flow does not have sufficient penetration ability and will not enter a vessel.

It may seem that holding the device very close to the blood vessel may mitigate the power dissipation of a turbulent flow. But holding the device even adjacent to the tissue would not enable the use of turbulent flows for vessel sealing. Providing the necessary energy levels at a depth of 1-1.5 vessel diameters requires placing the device so close that the vessel opening and surrounding tissue would vaporize. Even assuming that vaporization would not occur, such an attempt to direct a turbulent flow into the vessel would only heat the vessel walls close to the dissection surface, due to a large dynamic pressure gradient. Penetration of the plasma into the vessel for such a flow would not occur. Experiments confirm that only laminar or substantially laminar flows are capable of vessel sealing.

A laminar plasma flow with suitable dynamic pressure may be obtained over a range of temperatures and flow rates. For the plasma flows within the preferred ranges of temperature (12.5-15.5 kK) and room-temperature argon flow rate (0.25-0.5 L/min) the plasma flow is laminar. In addition to the ability to penetrate into the vessel, the plasma flow has to retain enough energy to both heat the vessel walls and evaporate an incoming fluid flow. The following discussion of energy requirements assumes the vessel is a blood vessel and the incoming fluid is blood. Nevertheless, this fluid may be lymph, bile, or any other fluid carried by a vessel in the body. In the case where the vessel carries a gas, no heat is required to evaporate an incoming fluid, but the plasma flow must still retain enough heat to heat the vessel walls.

As mentioned above, in the context of a single vessel, the blood flow rate can be expressed in mm/s. A typical blood flow rate is approximately 1 mm/s. It is known that an energy flux of 2.3 W/mm² is required to evaporate an incoming blood flow rate of 1 mm/s. These values are used for illustration, however, and as explained below, the vessel sealing method is capable of sealing vessels in which the flow rate is up to 4 mm/s.

Turning again to FIG. 7, as the plasma flow traverses along its path, the temperature of the plasma decreases due to three factors. These factors include (1) conduction of heat to surrounding air 76, (2) collisions between the plasma and air molecules, and (3) transfer of heat to blood vessel walls 75. For a vessel with a typical blood flow rate, the heat flux of plasma at incoming blood flow edge 77 has to be at least 2.3 W/mm² to ensure evaporation of the incoming blood. If the plasma heat flux is lower, then equilibrium of the rate of blood supply and the rate of its evaporation will occur at a depth smaller than 1-1.5 times the diameter and the vessel sealing may not occur.

Temperature decrease due to the first two factors occurs as the plasma propagates distance 72 from device tip 74 to the plane of dissection through air 76. This distance 72 is 10-30 mm, preferably 17.5-25 mm. Temperature decrease due to the heating of blood vessel walls 75 occurs inside the blood vessel.

The temperature decrease of the plasma flow can be modeled according to the following equation:

$$\rho u C_p \frac{\partial T}{\partial z} = \frac{1}{r}\frac{\partial}{\partial r}\left(\lambda r \frac{\partial T}{\partial r}\right) + \frac{3}{2}\delta v n_{air} k_B (T_{air} - T) + \alpha(T - T_W).$$

In the above equation, all variables without indices refer to plasma properties. Specifically, in the above equation $\rho$ is the density in kg/m³, u is the velocity in m/s, $C_p$ is the heat capacity in J/(kg×K), r is the radius in m, $\lambda$ is the heat conductivity W/(K×m), $\delta$ is the part of energy transferred between particles in collisions and is dimensionless, $v^v$ is the collision frequency in $s^{-1}$, n is the number density in particles/m³, $k_B$ is the Boltzmann constant in J/K, $\alpha^\alpha$ is the heat transfer coefficient in W/(m³×K), T is the temperature in K, and z is the distance in m from the tip 74 of the device along axis 78 of the plasma flow. In the above equation, the term on the left hand side, $$\rho u C_p \frac{\partial T}{\partial z},$$

represents the temperature decrease as the plasma propagates away from the device. Each term on the right hand side accounts for a different heat loss factor.

The first term on the right hand side, $$\frac{1}{r}\frac{\partial}{\partial r}\left(\lambda r \frac{\partial T}{\partial r}\right),$$

accounts for the conduction of heat to surrounding air 76. Some embodiments of the plasma surgical device suitable for coagulation generate plasma flows with a substantially parabolic temperature distribution. For such plasma flows, the first term on the right side of the equation is reduced to $$-\frac{4\lambda}{R^2}T,$$

where R is the radius of the plasma flow. From this equation it is seen that heat loss due to heat conduction to the air 76 is inversely proportional to the diameter of the plasma flow squared. This means that the temperature of a plasma flow discharged from a 0.5 mm device decreases more rapidly with increasing distance z than a plasma flow discharged from a 0.8 mm device, if all other plasma properties are the same.

The second term accounts for energy loss due to collisions of the plasma and air molecules. The key parameter for this factor is the collision frequency v expressed as follows:

$$v = \frac{v_{air}\rho(T)}{m_p A_{ar}} Q_{\frac{air}{argon}},$$

where: $V_{air}$ is the relative mean speed in m/s, $\rho(T)$ is the density in kg/m³, $m_p$ is the proton mass in kg, $A_{ar}$ is the atomic (molecular) weight which is dimensionless, and $$Q_{\frac{air}{argon}}$$

is the collision cross section in m².

The collision frequency is proportional to the density of plasma, which in turn is a function of the temperature. Referring to Table 1, for argon, the density decreases substantially exponentially with temperature. For example, argon at room temperature has the density of 1.6794 kg/m³, at 5 kK, the density is 0.0974 kg/m³, at 10 kK, the density is 0.0474 kg/m³, and at 15 kK, the density is 0.0208 kg/m³. From this temperature-density relationship, it follows that molecules of higher temperature plasma have fewer collisions with air molecules. A higher temperature plasma results in less heat loss due to air molecule collisions.

The third term represents cooling of the plasma flow due to contact with vessel walls 75. In the air, this term is zero, while inside the vessel it accounts for a significant source of temperature loss. The temperature of the plasma flow decreases rapidly inside the vessel. Importantly, the heat transferred to the vessel walls is what causes the denaturation of collagen and ultimate occlusion. At incoming blood flow edge 77, the heat flux that should remain in the plasma flow is 2.3 W/mm² for a typical blood flow rate of 1 mm/s. This heat evaporates incoming blood 73. A higher blood flow rate will require a higher heat flux.

Figure 12:
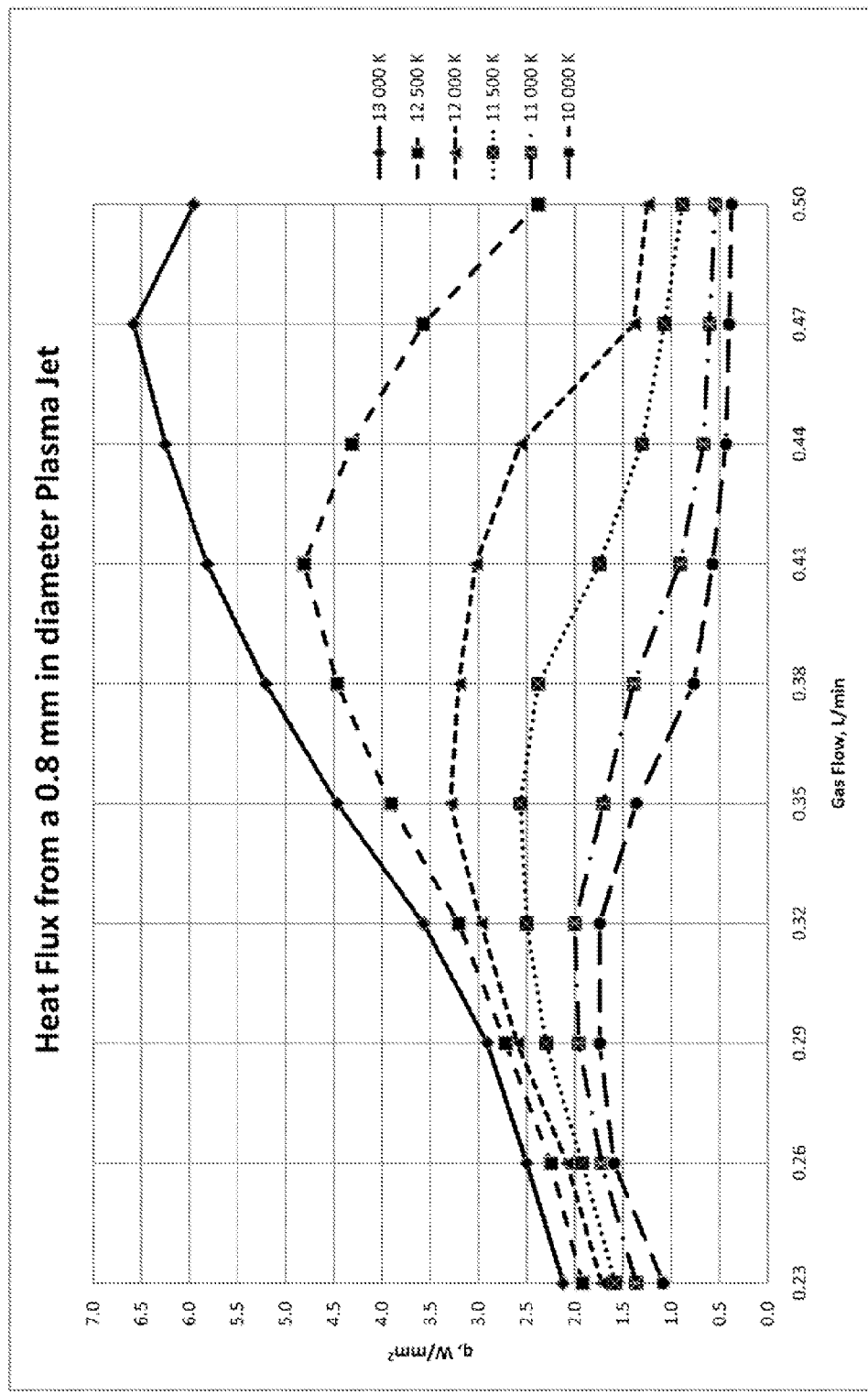
FIG. 12 illustrates the heat flux at a distance of 15 mm for various temperatures and gas flow rates.

Taking into account general characteristics of the plasma flow for vessel sealing (i.e., ability to penetrate and retain sufficient heat), experiments were performed to determine what temperature and flow rate characterize the desired plasma flow. FIG. 12 shows real measurements of heat flux at 15 mm from a 0.8 mm plasma surgical device plotted as a function of room-temperature plasma-generating gas flow for a series of initial temperatures. In the particular embodiment of the device used for this experiment, the heating portion diameter was 0.4 mm and the plasma channel length was 2.5 mm. As gas flow increases for a given temperature the heat flux increases up to a peak. Increasing the gas flow beyond this peak results in a reduction of the heat flux despite increasing the power of the device near its tip. The reason for this is believed to be the onset of turbulent flow characteristics such as mixing with air and divergence of the plasma flow. For higher temperatures, this peak heat flux occurs for higher gas flow rates, because of the increased enthalpy and lower density of the high-temperature plasma flow.

To be capable of evaporating a typical bleeding rate of 1 mm/s, the plasma flow must have a heat flux at the surface of the vessel substantially greater than 2.3 W/mm$^2$. From FIG. 12, it can be observed that a plasma discharged from the device with a temperature over 12.5 kK delivers a heat flux substantially greater than 2.3 W/mm$^2$ over a wide range of gas flow levels at a distance of 15 mm. Temperatures 11.5 kK and below will not reach the required heat flux at this distance, or if they do it will be over an extremely narrow range of possible gas flows. Accordingly, the temperature of 12.5 kK or above is preferable. In some cases, however, even plasma with the initial temperature of 11 kK was shown to seal relatively small vessels with relatively low blood flow rates.

Figure 13:
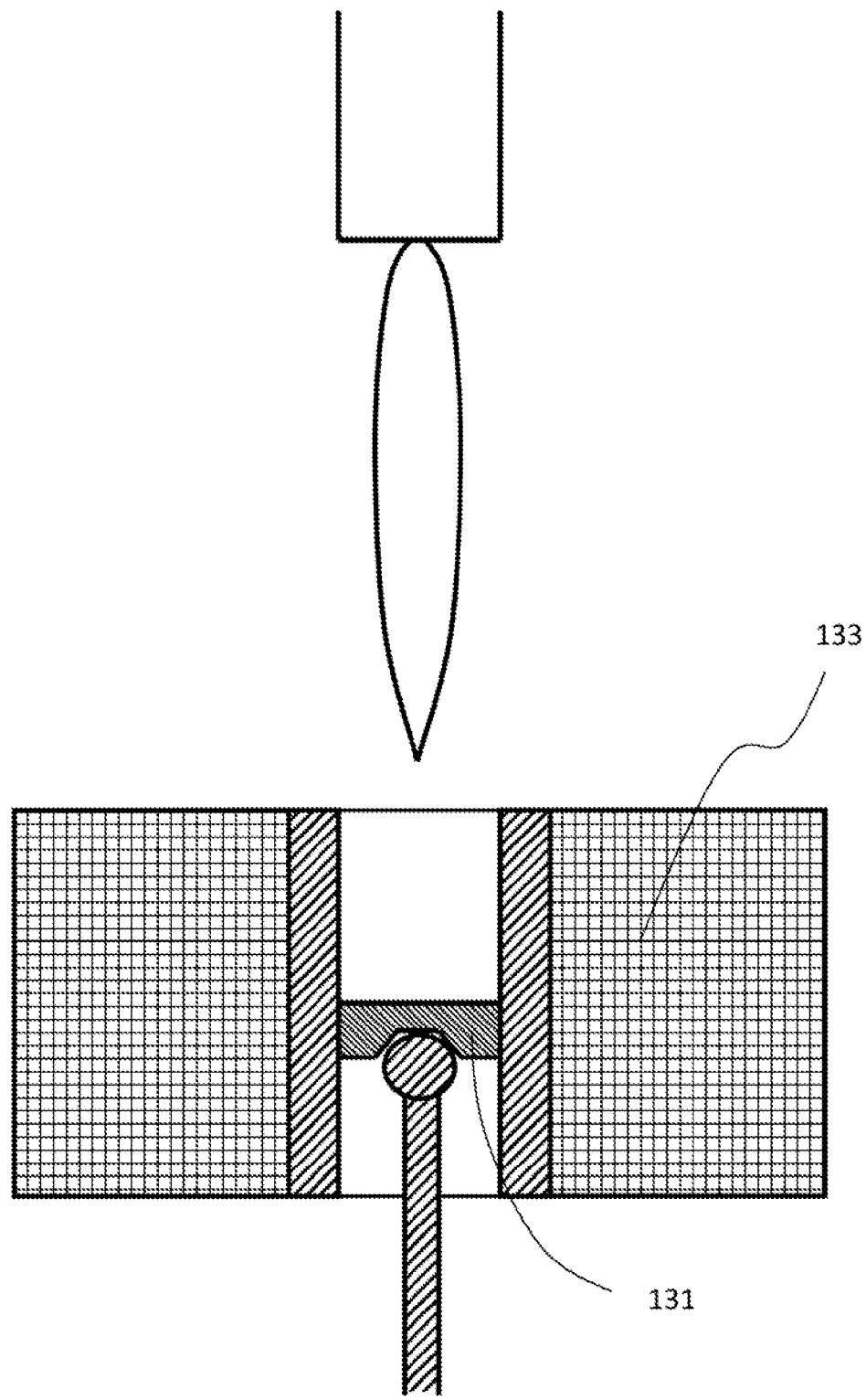
FIG. 13 illustrates an experimental setup for measuring the heat flux within a ceramic vessel.
Figure 14:
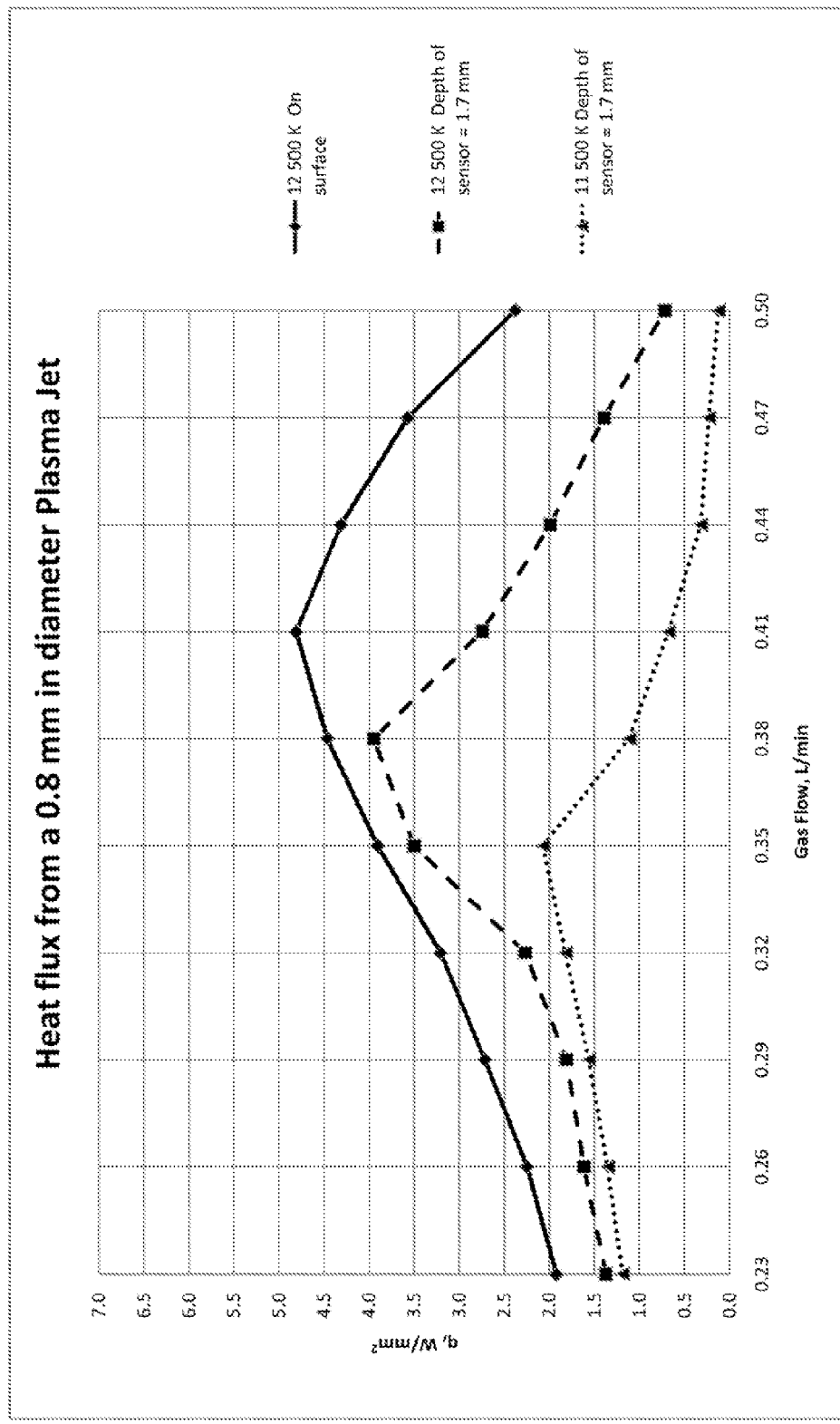
FIG. 14 illustrates the heat flux achieved for various gas flows, temperatures, and positions of a sensor.

Having determined the suitable initial temperature range of the discharged plasma for vessel coagulation, the optimal flow rate of argon has to be determined. FIG. 13 shows an experimental setup that models the vessel sealing environment. In the experiment shown in FIG. 13, the heat flux sensor 131 is placed in a tube 133 with a diameter of 1.7 mm at a depth of 1.7 mm from the surface. By varying the room-temperature argon flow rate, it was observed which flow rate produces heat flux of 2.3 W/mm$^2$ or above at the depth of 1.7 mm, after the plasma flow traversed 15 mm of air. FIG. 14 shows the results of this experiment.

Qualitatively, FIG. 14 shows that inside the vessel the heat flux peaks for lower gas flow than in the air. The magnitude of this peak heat flux is also significantly lower, due to heat transfer to the vessel walls. At an initial temperature of 12.5 kK, for example, the peak heat flux occurs at a gas flow of 0.41 L/min at the surface but peaks at 0.38 L/min inside of the vessel. Above the gas flow rate of 0.38 L/min the penetration ability of the plasma flow inside the blood vessel decreases significantly and drops below 2.3 W/mm$^2$ for flows over approximately 0.43 L/min.

Plasma flow with the initial temperature of 12.5 kK occurs at approximately 8.5-9 A, which is considered a safe operating current. For all embodiments, temperatures in the range of approximately 12.5-15.5 kK that have been shown to seal vessels, the operating current is 8.5-10 A.

To accomplish sealing with a plasma flow with the initial temperature of 12.5 kK, the room-temperature plasma-generating gas flow should be the range of 0.33-0.42 L/min, preferably 0.35-0.38 L/min. For comparison, FIG. 14 also shows the heat flux of the plasma flow with the initial temperature of 11.5 kK at the depth of 1.7 mm. For a plasma flow with initial temperature of 11.5 kK the heat flux is under 2.3 W/mm$^2$ for any flow rate. Therefore, a plasma flow with initial temperature of 11.5 kK is unsuitable for sealing a 1.7 mm blood vessel from the distance of 15 mm.

In the embodiments used for sealing gas-carrying vessels, such as bronchi in lung tissue, no incoming fluid flow is evaporated, and therefore the heat flux inside the vessel can be lower. In those embodiments, an argon flow rate of approximately 0.12-0.37 L/min, preferably 0.23-0.26 L/min at room temperature is used.

Figure 15:
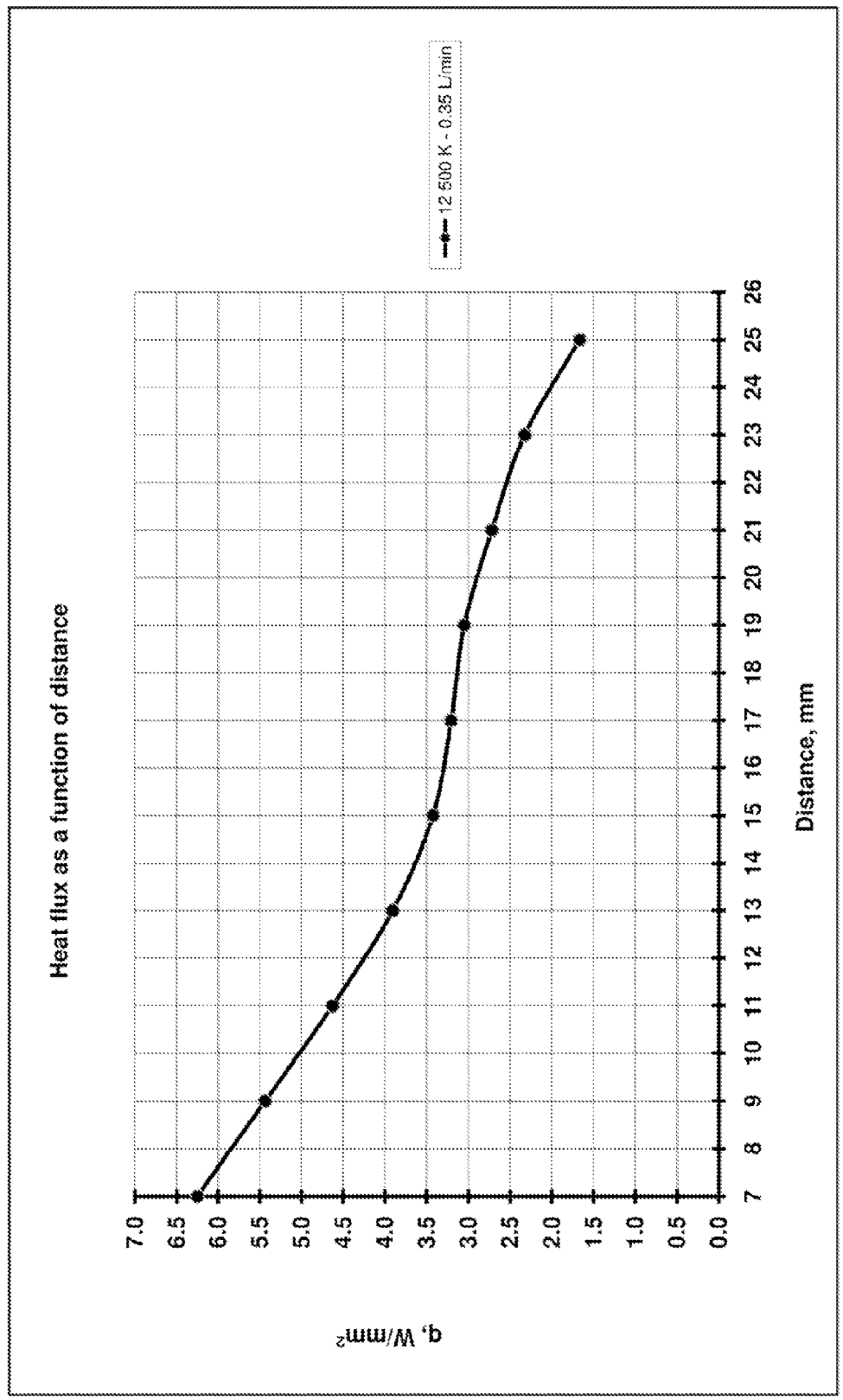
FIG. 15 illustrates the heat flux achieved at various distances from a plasma generating device.

Experiments confirmed that plasma flow with the initial temperature of 12.5 kK and the flow rate of 0.33-0.42 L/min achieved a power of 20-60 W at the surgical site, considered to be suitable for blood vessel sealing. The initial power level of the plasma flow, which is the power achieved immediately after the plasma flow is discharged, can be calculated with the following equation:

$$P = E \times F_{Plasma},$$

where P is the power (W), E is the enthalpy (J/kg), and $F_{Plasma}$ is the mass flow rate (kg/s). This initial power level is calculated using the flow rate of hot plasma leaving the device. However, the power level at the surgical site is significantly lower than the initial power level due to the interaction of the plasma flow with surrounding air. FIG. 15, discussed in greater detail below, shows the relationship of the heat flux of a plasma flow and the distance from the plasma-generating device. Power is proportional to heat flux, so FIG. 15 is indicative of power dissipation as the plasma flows away from the device.

The above discussion focused on typical vessels of under 1.7 mm in diameter and with the fluid flow rate of 1 mm/s. For larger vessels having higher fluid flow rates, achieving a heat flux greater than 2.3 W/mm$^2$ at a distance greater than 1.7 mm inside the vessel is required. The largest vessels for which this method has been found to be effective are blood vessels that have a diameter of 4 mm, with a maximum blood flow rate of 4 mm/s. In the preferred embodiment, given that the initial temperature of the plasma and the flow rate are fixed, the operator may influence the depth of penetration of the plasma flow inside the vessel being sealed by changing the working distance of the device from the opening of the vessel. This allows the operator to seal different vessels during the same procedure by simply moving the device closer or farther apart depending on the vessel size and blood flow rate.

This is possible because moving the device closer to the surface of dissection results in increased penetration of the plasma flow and increased heat flux at the desired depth. Consequently, even though it may be possible to achieve sealing of some vessels with a lower initial temperature (e.g. 12 kK or even 11 kK), the usability of such a procedure is reduced significantly for larger vessels with higher fluid flow rates. For these vessels, the distance may have to be decreased so much as to create a significant risk of accidental tissue vaporization.

Operational temperature of at least 12.5 kK ensures that the device does not have to be held closer than approximately 10 mm from tissue. FIG. 15 shows heat flux as a function of distance from the device tip for a plasma flow with initial temperature of 12.5 kK and gas flow rate of 0.35 L/min. For a plasma flow with these characteristics used to send a blood vessel, a distance of 10-15 mm will accomplish vessel sealing for a high level of bleeding, 15-20 mm will accomplish sealing for a moderate level of bleeding, and 20-30 mm will accomplish vessel sealing for a low level of bleeding.

Another safety aspect is ensuring that a dangerous condition called gas embolism, which is the result of gas bubbles entering the blood stream, does not happen as a result of vessel sealing procedures. Embolism can cause the stoppage of blood flow, which can lead to heart attacks, stroke, and even death. Blood embolism can occur during any surgery in which a blood vessel is open and a pressure gradient exists favoring entry of a gas into the blood vessel. Directing plasma at a blood vessel may appear to create an increased chance of embolism. However, for the methods of vessel sealing disclosed herein, embolism is virtually impossible.

To explore the possibility of embolism as a result of plasma blood vessel sealing, the concept of backpressure is introduced. With reference back to FIG. 7, backpressure refers to the pressure inside portion 81 of the blood vessel free of blood due to the presence of cooled plasma-generating gas and blood vapors. When plasma flow 79 is directed into the blood vessel, incoming blood 73 evaporates. As this happens, the plasma flow cools down and turns into argon gas. Gas mixture 80 comprises this cooled argon gas and the blood vapors. This gas mixture 80 may stagnate inside portion 81 of the blood vessel. Plasma flow 79, which has an associated dynamic pressure, must overcome the opposing force from the backpressure exerted by the cooler gas mixture 80. The amount of backpressure that plasma flow 79 experiences depends on the densities of plasma flow 79 that enters the vessel and gas mixture 80. If cooled gas mixture 80 is significantly denser than plasma flow 79 the backpressure is low. Assuming that the cooled plasma and blood vapors escape the vessel at approximately 100° C. which is 373 K, the ratio of densities, based on Table 1, is greater than 30. With this ratio no significant back pressure is experienced by the hot plasma flow.

On the other hand, the pressure of the plasma flow must be less than the blood pressure in the blood vessel. For reference, the minimum pressure in portal venous, 6.67 mbar, is taken. If the pressure of the plasma flow as it enters the vessel is greater than the minimum portal venous pressure, there is at least a risk of the plasma entering the blood stream. Accordingly, it is preferable that the backpressure is significantly lower than the minimum portal venous pressure. This allows for a range of dynamic pressures of the plasma flow that would overcome the backpressure, but at the same time would be under the minimum portal venous pressure. An unacceptable condition occurs when the backpressure is higher than the minimum portal venous pressure.

Figure 16:
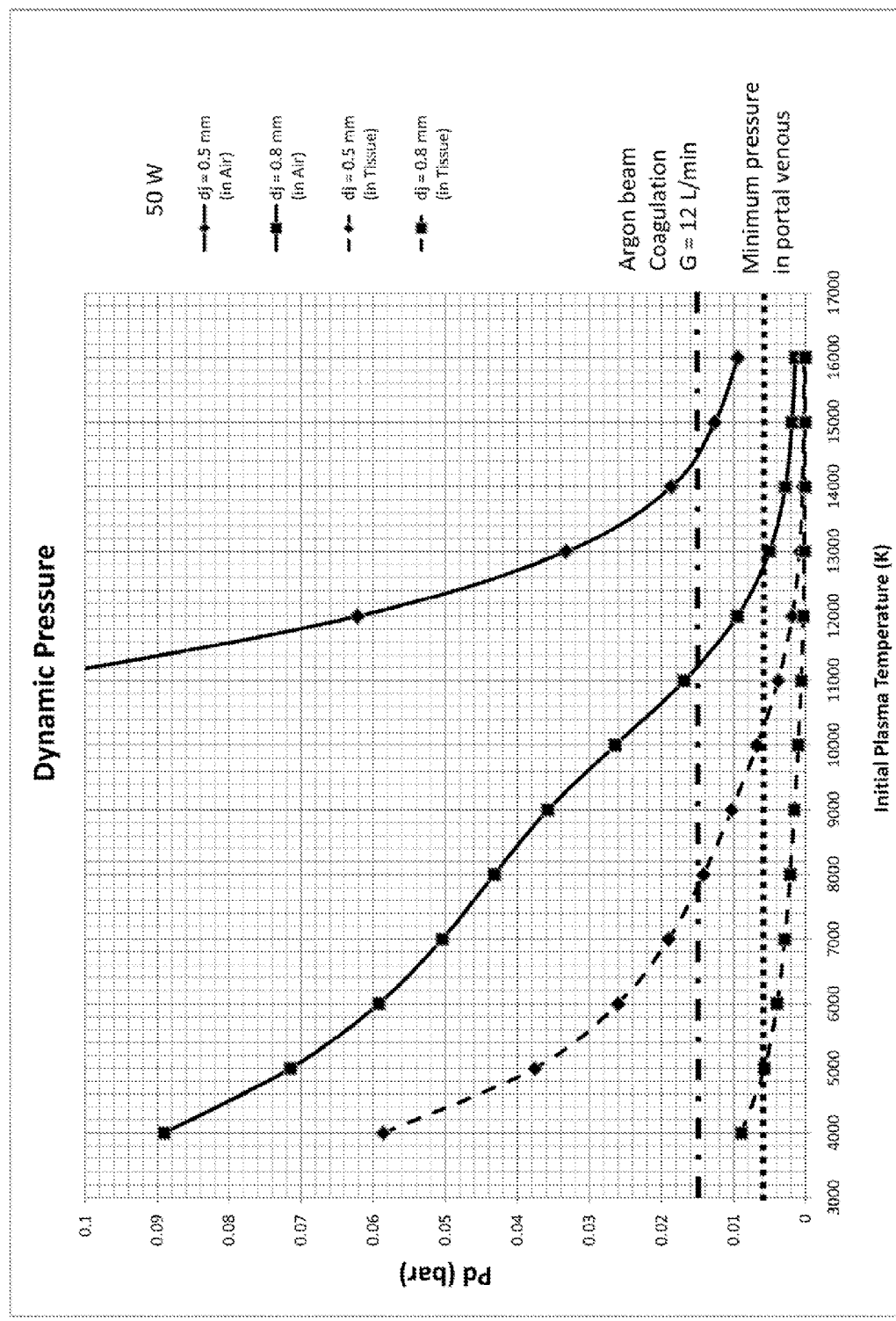
FIG. 16 illustrates the backpressure inside a blood vessel for various temperatures.

FIG. 16 shows the backpressure observed for a series of procedures with the discharged plasma having different initial temperatures while maintaining a constant power level of 50 W at the surgical site. Two devices, a 0.5 mm and a 0.8 mm device, were used. The two solid curves show the dynamic pressure of the devices measured before entering the surgical site, while the two dotted curves show the backpressures experienced inside the vessel. FIG. 16 shows that for the plasma flow with the initial temperature of 12.5 kK, backpressure is essentially zero for all embodiments of the device operated with the power of 50 W. This ensures that there is a relatively large range of available dynamic pressure that does not create any risk of embolism.

During surgery it is possible for an operator to accidentally allow the device tip to get too close to the vessel opening, even possibly momentarily placing the tip directly onto the opening end of the vessel. It is desirable to ensure that even if this occurs there is no risk of gas embolism. In the preferred embodiment, where a temperature of 12.5-13 kK is used with a 0.8 mm device, the dynamic pressure of the plasma flow as it exits the device is lower than the portal venous pressure. Therefore, even if this device is accidentally brought into close proximity of the vessel opening, there is no possibility of gas embolism.

FIG. 16 also shows the pressure of argon beam coagulator, a prior art device that performs coagulation using room-temperature argon beam with the flow rate of 12 L/min. As seen from FIG. 16, there is a significant risk of gas embolism associated with the use of such a device. A proper use of high-temperature plasma, in contrast, eliminates this risk completely.

Figure 17:
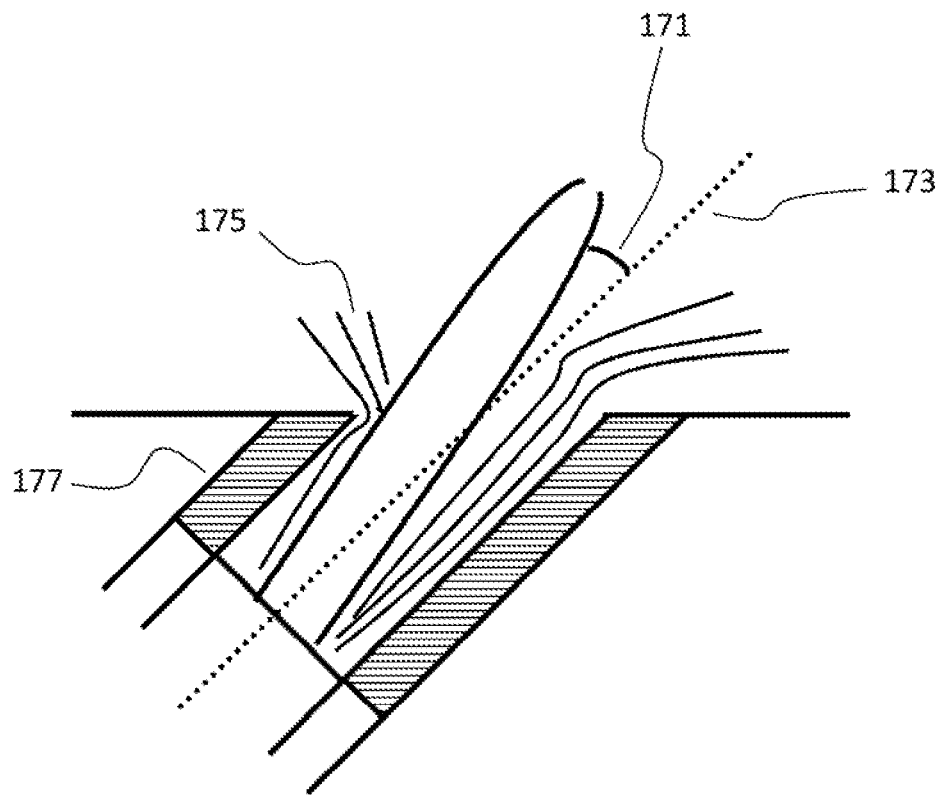
FIG. 17 illustrates a plasma flow directed at an angle into a blood vessel.

As shown in FIG. 17, the plasma flow has a trajectory that forms an angle of less than 20°, preferably less then 10°, with the axis of the vessel 173 at the surgical site. This ensures that cooled argon gas 175 escapes along the periphery of vessel walls 177 and that the plasma penetrates deeply enough into the vessel to create a strong seal.

Taking the above considerations into account, device settings and plasma characteristics have been calculated to achieve sealing for vessels up to 4 mm in diameter while maintaining a high level of safety. Table 2 summarizes parameters of different devices required for sealing a 2 mm vessel with a 1 mm/s flow rate. Table 3 summarizes parameters of these devices required for sealing a 4 mm vessel with a 4 mm/s flow rate.

TABLE 2

2 mm vessel diameter; 1 mm/s blood flow rate

| Device | Current (A) | Flow rate (L/min) | Init. T (kK) | Power (W) | Distance from Tissue (mm) | Heat flux at 1.5 × d inside vessel (W/mm²) |
|---|---|---|---|---|---|---|
| 0.5 mm | 8.5-10 | 0.25-0.35 | 12.5-14 | 20-35 | 15-20 | 2.0-3.5 |
| 0.8 mm | 8.5-10 | 0.3-0.4 | 12.5-14 | 20-40 | 17.5-25 | 2.0-3.5 |
| 1.2 mm | 8.5-10 | 0.35-0.5 | 12-14 | 20-50 | 22.5-30 | 2.0-3.5 |

TABLE 3

4 mm vessel diameter; 4 mm/s blood flow rate

| Device | Current (A) | Flow rate (L/min) | Init. T (kK) | Power (W) | Distance from Tissue (mm) | Heat flux at 1.5 × d inside vessel (W/mm²) |
|---|---|---|---|---|---|---|
| 0.5 mm | 8.5-10 | 0.25-0.35 | 14-15.5 | 35-50 | 10-15 | 3.5-5.0 |
| 0.8 mm | 8.5-10 | 0.3-0.4 | 14-15.5 | 40-60 | 10-17.5 | 3.5-5.0 |
| 1.2 mm | 8.5-10 | 0.35-0.5 | 14-15.5 | 50-80 | 15-22.5 | 3.5-5.0 |

As to the duration of vessel sealing procedure, the time required for vessel sealing is limited by heat diffusion through the vessel walls and surrounding tissue. When the plasma flow enters inside a typical vessel, the heat is transferred to the vessel walls and to the surrounding tissue through the vessel walls. To accomplish sealing, heat from the plasma flow has to transfer to the vessel walls and to the tissue adjacent the vessel walls. For a typical vessel the penetration of heat sufficient to denature collagen to the distance of 1 mm is sufficient for sealing. The distance of penetration of heat into tissue by diffusion sufficient to denature collagen can be estimated as:

$$L=\sqrt{4kt}$$

where k is the thermal diffusivity of tissue, which is approximately $1.4 \times 10^{-7}$ m²/s. For plasma flow with characteristics suitable for vessel sealing, it takes approximately 2 s to denature collagen in a 1 mm-thick layer, which includes the vessel wall and surrounding tissue.

Figure 18A:
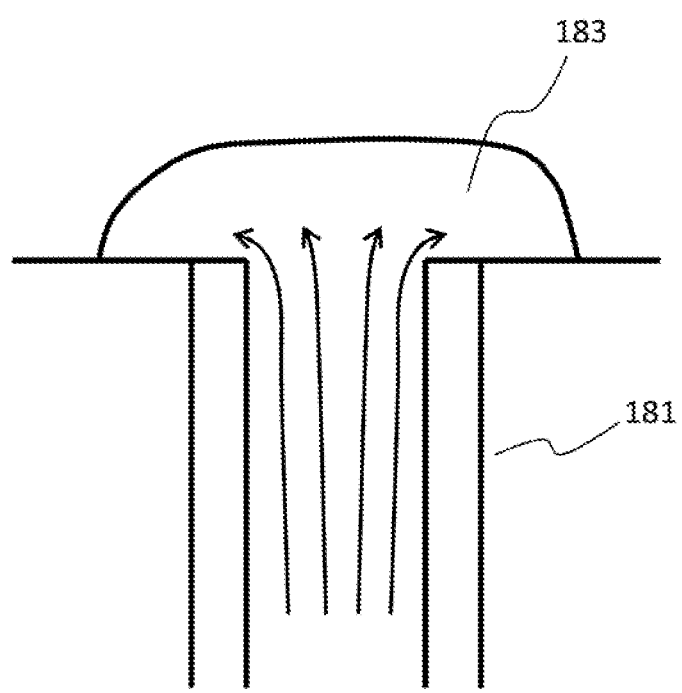
FIGS. 18A-18G illustrate a sequence depicting the method as it is performed.

FIGS. 18A-F show in sequence the sealing of a blood vessel in accordance with the preferred embodiments. FIG. 18A shows a blood vessel 181 that has been severed during the surgery prior to the operator generating and directing plasma into the vessel. Blood 183 continues to flow from vessel 181 until the vessel is sealed.

Figure 18B:
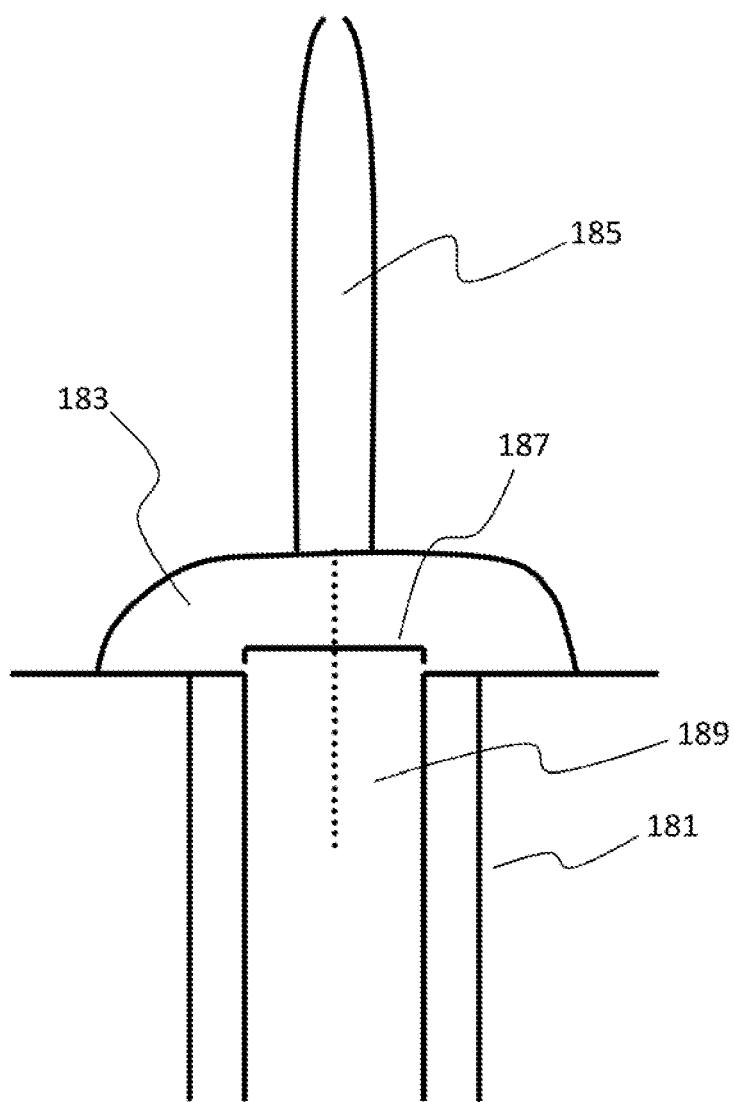

FIG. 18B shows a generated plasma flow 185 directed into opening end 187 of vessel 181 just before plasma flow 185 reaches blood 183. Plasma flow 185 has a trajectory substantially aligned to axis 189 of the blood vessel at opening end 187. Plasma flow 185 is laminar with a temperature between about 12.5-15.5 kK.

Figure 18C:
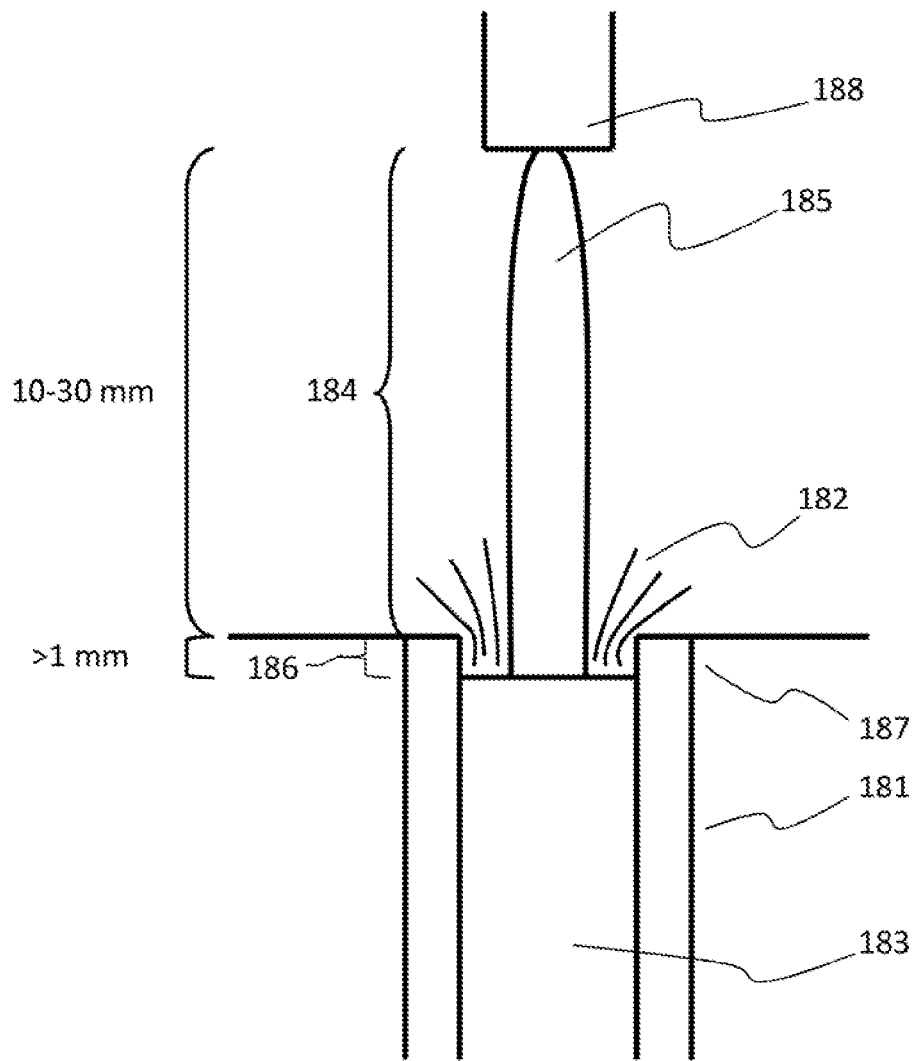

FIG. 18C shows plasma flow 185 evaporating blood 183 from blood vessel 181. As plasma flow 185 heats blood 183, a gas mixture 182 comprising blood vapors and cooled argon gas builds up around opening end 187 of vessel 181. Because of the parabolic temperature distribution of plasma flow 185, gas mixture 182 is pushed to the periphery of the blood vessel and out of the opening end. At opening end 187, plasma flow 185 has a relatively low density due to its high temperature. Gas mixture 182, in contrast, has a temperature of approximately 100° C. and therefore it has a significantly higher density. Because the ratio of the density of gas mixture 182 to the density of plasma in the plasma flow 185 is large, the backpressure present in blood vessel 181 is small. The small backpressure ensures that the dynamic pressure of plasma flow 185 overcomes the backpressure and enters the blood vessel. The dynamic pressure, while large enough to overcome the backpressure, is still below the blood pressure and therefore the chance of gas embolism is low.

Further, FIG. 18C shows insufficient penetration of the plasma flow into blood vessel 181. The working distance 184 of the plasma device has not been adjusted to accomplish blood vessel sealing. Depth of penetration 186 is less than the 1-1.5 vessel diameters required for sealing. At this working distance, too much heat is lost as the plasma propagates from tip 188 to the opening end 187 of the blood vessel, and the penetration ability of the plasma flow is therefore too low. The heat flux required to evaporate blood 183 can only be achieved close to opening end 187.

Figure 18D:
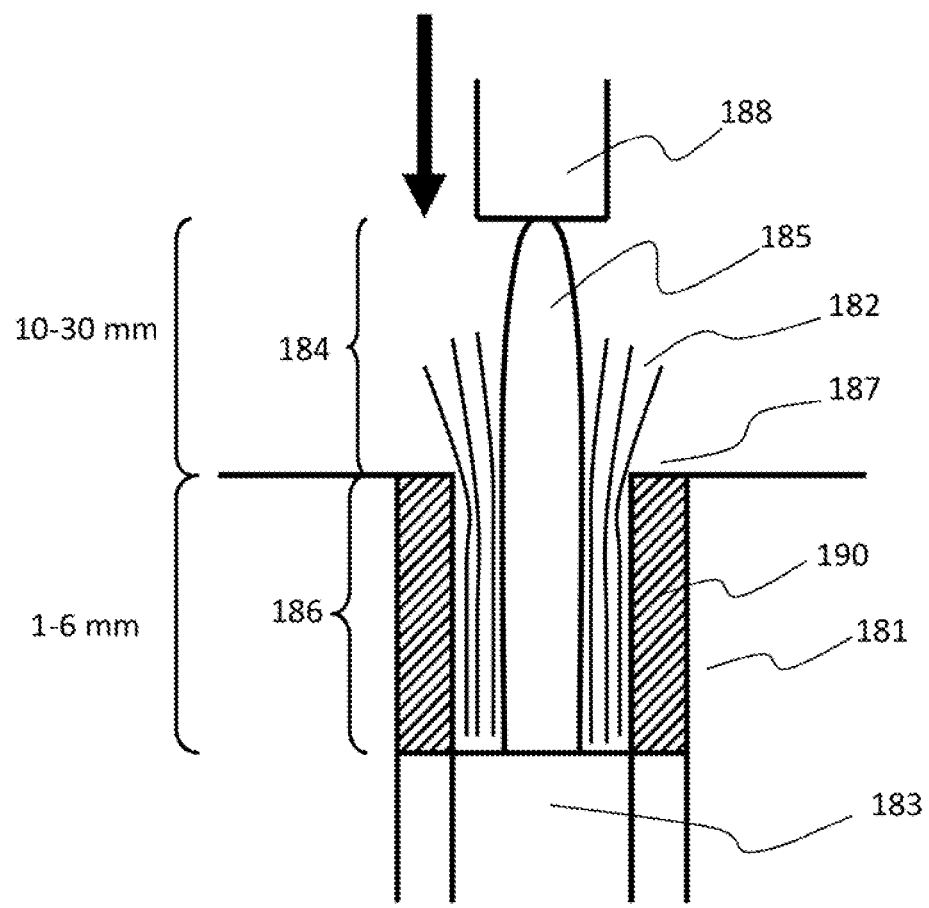

FIG. 18D, in contrast, shows sufficient penetration of plasma flow into blood vessel 181. Working distance 184 has been decreased, reducing the heat lost before reaching opening end 187. Consequently, the penetration ability of plasma flow 185 is high enough to achieve depth of penetration 186 which is between 1-1.5 vessel diameters. As plasma flow 185 propagates inside blood vessel 181 heat is transferred to blood vessel walls 190.

Figure 18E:
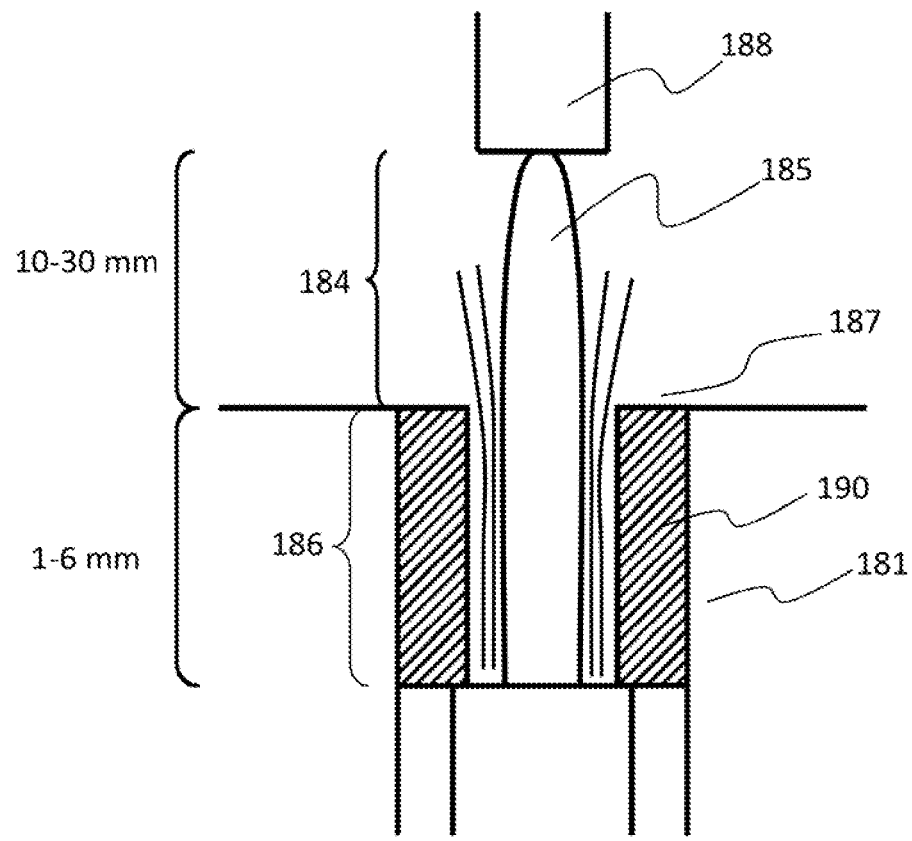

Once the required depth of penetration 186 has been achieved, the working distance 184 is maintained as the plasma flow continues to be directed into the vessel and as it evaporates blood 183 as the blood flows toward opening end 187. This position is held for about 1-1.5 s for vessels of diameter less than 3 mm, or for 1.5-2 s for vessels of diameter greater than 3 mm. FIG. 18E shows blood vessel 181 after enough heat has been transferred to walls 190 to begin contracting the vessel walls. The collagen present in walls 190 has begun to denature and partially occlude the vessel.

Figure 18F:
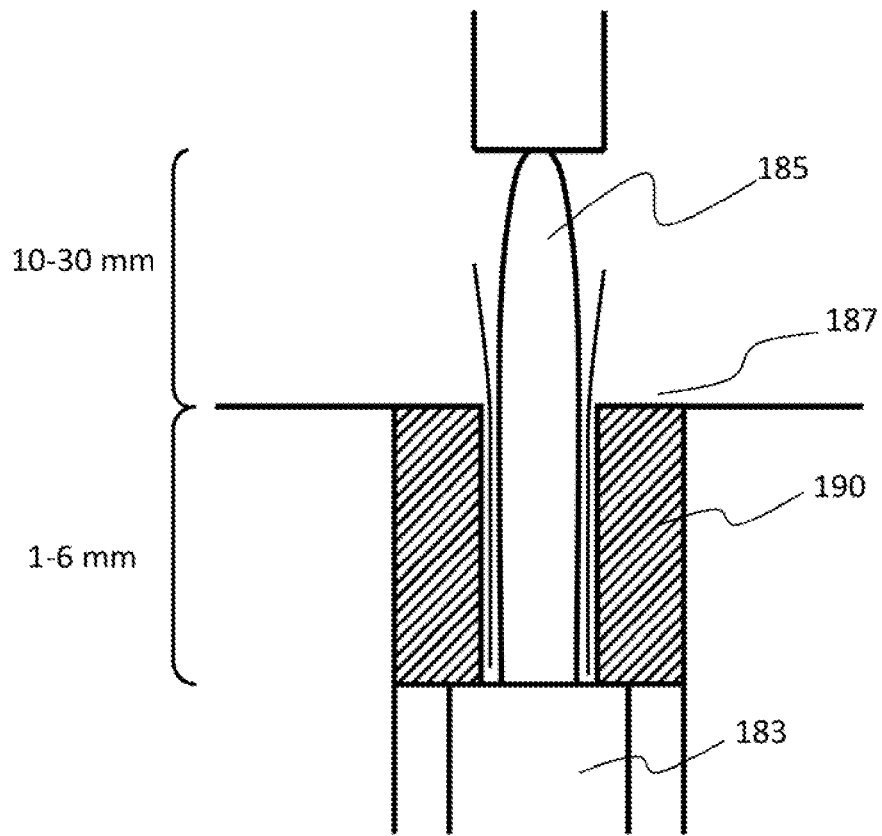

FIG. 18F shows the nearly complete contraction of blood vessel walls 190. Plasma flow 185 continues to evaporate blood 183 flowing towards opening end 187. Concurrently, heat continues to be transferred to walls 190 and they continue to contract until a complete seal is formed.

Figure 18G:
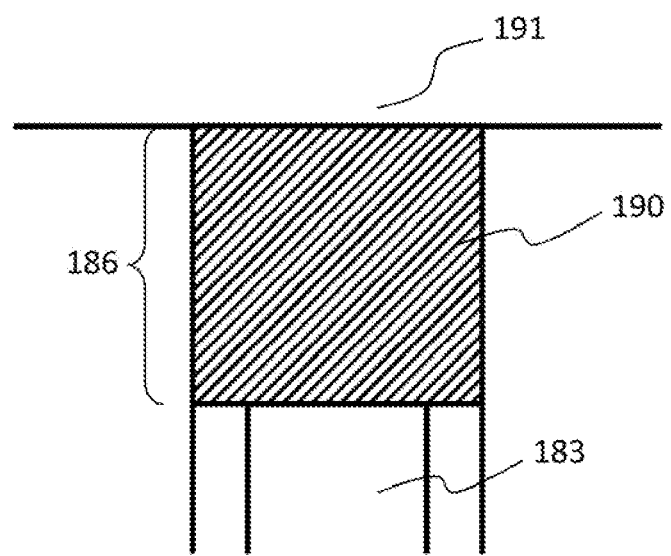

Finally, FIG. 18G shows seal 191 formed from walls 190. The plasma flow has been moved away from the sealed vessel. Because the depth of penetration 186 of the plasma flow was deep enough, seal 191 is thick enough and strong enough to withstand the pressure of blood 183.

Figure 19:
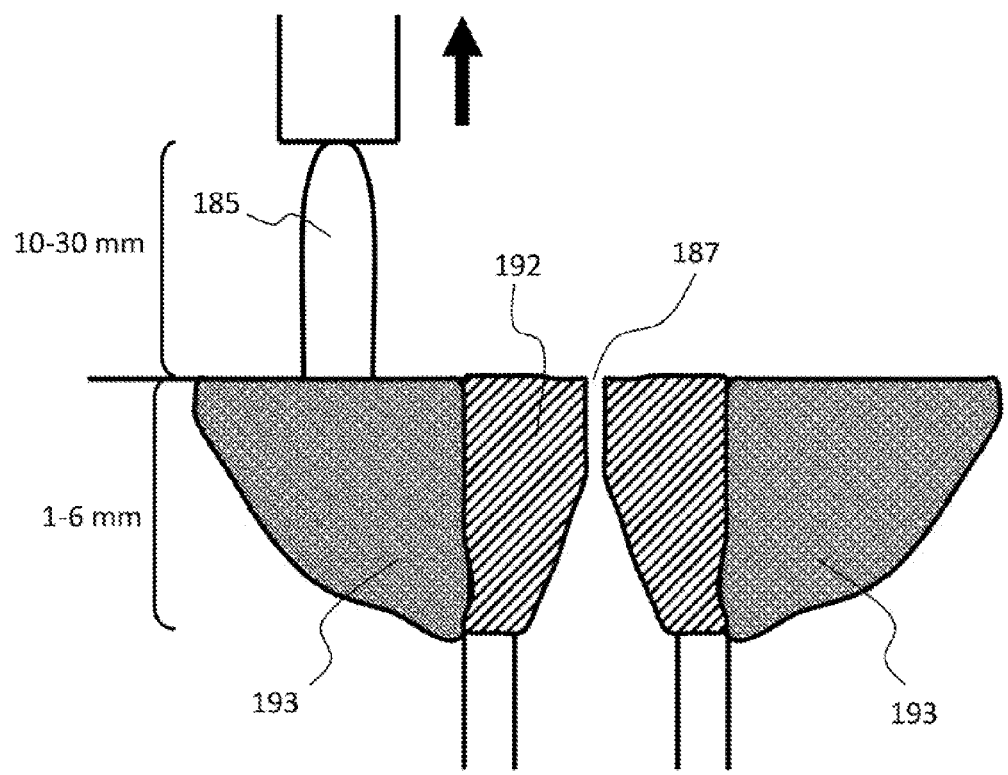
FIG. 19 illustrates an optional step for further contracting large blood vessels.

An optional step performed for vessels with the diameter greater than 3 mm is shown in FIG. 19. Here, a blood vessel was not completely occluded despite accomplishing swelling of the collagen in the blood vessel walls. This may occur because the diameter of the blood vessel is simply too large to be occluded by swollen walls 190 alone. FIG. 19 shows that for complete occlusion, opening 187 should be sealed. The blood vessel walls can be further contracted by swelling surrounding tissue 193. After contracting the blood vessel walls 190 with a plasma flow 185 directed into the vessel, the same plasma flow is directed at surrounding tissue 193. Denaturing collagen in surrounding tissue 193 causes swelling, and this swelling pushes the vessel walls 192 inward, to completely contract and close opening 187. By "sweeping" the tissue surrounding the vessel in a circular motion, a robust seal 190 (shown in FIG. 18G) can be formed even for greater-3 mm-diameter blood vessels. Circular "sweeping" may be accompanied with increasing the distance from the plasma-generating device to the tissue, especially if the distance was decreased to achieve sufficient penetration, as discussed in connection with FIG. 18C.

Figure 5:
FIG. 5 illustrates an actual vessel of diameter 3.5 mm sealed according to the method disclosed herein.

FIG. 5 shows a scaled view of a real blood vessel with a diameter of 3.5 mm that has been sealed in accordance with the preferred embodiment. Seal 201 completely occludes vessel 202, preventing further blood flow.

The method as illustrated in FIGS. 18A-G and 19 is also effective for other types of vessels. Fluid carrying vessels, such as bile ducts and lymph vessels, will also have a fluid flow which must be evaporated as in the case of blood vessels. Gas carrying vessels, such as bronchi in lung tissue, will not have a fluid flow and therefore have a smaller gas flow or power requirement. Regardless of the type of vessel, however, the initial temperature of at least 11 kK, but preferably 12.5-15.5 kK is required to achieve penetration of the plasma flow into the vessel.

The embodiments of the vessel sealing method are equally effective for veterinary applications.

The foregoing description of the embodiments of the present invention has been presented for the purposes of illustration and description. It is not intended to be exhaustive nor to limit the invention to the precise form disclosed. Many modifications and variations will be apparent to those skilled in the art. The embodiments were chosen and described in order to best explain the principles of the invention and its practical applications, thereby enabling others skilled in the art to understand the invention. It is intended that the scope of the invention be defined by the accompanying claims and their equivalents.

What is claimed:

1. A method of sealing an opening of a liquid-carrying vessel in a living organism, comprising:
   a. directing a plasma flow into an opening end of the liquid-carrying vessel;
   b. evaporating a liquid from a portion of the liquid-carrying vessel with the plasma flow, wherein the portion extends from the opening end of the liquid-carrying vessel to a depth equal to at least the liquid-carrying vessel diameter;
   c. contracting the walls of the liquid-carrying vessel in the portion of the liquid-carrying vessel from which the liquid is evaporated by heating the walls; and
   d. forming a seal from the contracted walls of the liquid-carrying vessel, wherein a diameter of the liquid carrying vessel is at least 1 mm.

2. The method of claim 1, further comprising generating the plasma flow with an initial temperature of at least 11 kK.

3. The method of claim 2, wherein the generated plasma flow has a diameter of at least 0.45 mm when discharged.

4. The method of claim 1, wherein the trajectory of the plasma flow is at an angle of less than 20° to an axis of the liquid-carrying vessel at the opening.

5. The method of claim 4, wherein the trajectory of the plasma flow is substantially aligned with the axis of the liquid-carrying vessel at the opening end.

6. The method of claim 1, wherein contracting the walls of the liquid-carrying vessel comprises denaturing collagen in the walls of the liquid-carrying vessel.

7. The method of claim 1, wherein at the opening of the liquid-carrying vessel the plasma flow is laminar.

8. The method of claim 7, wherein the plasma flow has a substantially parabolic temperature and velocity distribution at the opening of the liquid-carrying vessel.

9. The method of claim 2, wherein evaporating blood from the portion of the liquid-carrying vessel comprises cooling plasma from the plasma flow, and
    wherein the ratio of the density of the cooled plasma and the density of the plasma in the generated plasma flow is greater than 30.

10. The method of claim 1, further comprising directing the plasma flow to an area near the opening end of the liquid-carrying vessel.

11. A method comprising:
    a. discharging a plasma flow using a flow of a plasma-generating gas with a flow rate of 0.25-0.5 L/min at room temperature, the plasma flow having a diameter of at least 0.45 mm when discharged, the plasma flow having a temperature of at least 11 kK when discharged; and
    b. directing the plasma flow into an opening of a vessel having a diameter of at least 1 mm in a living organism.

12. The method of claim 11, further comprising directing the plasma flow at an area surrounding the opening of the vessel.

13. The method of claim 12, wherein directing the plasma flow at the area surrounding the opening of the blood vessel is performed with a substantially circular motion around the opening of the vessel.

14. The method of claim 11, wherein the vessel is a blood vessel.

15. The method of claim 11, wherein the plasma flow is discharged at a distance of 10-30 mm from the opening of the vessel.

16. The method of claim 15 further comprising, after directing the plasma flow into the opening of the vessel for at least 0.5 s, decreasing the distance.

17. The method of claim 12, wherein the plasma flow is directed into the opening of the blood vessel at an angle of at most 20° to the axis of the blood vessel at the opening.

18. A method of sealing a fluid-carrying vessel in a living organism, comprising:
    a. directing a plasma flow into an opening end of the fluid-carrying vessel;
    b. contracting walls of the fluid-carrying vessel; and
    c. forming a seal from the contracted walls of the fluid-carrying vessel, wherein a diameter of the fluid-carrying vessel is at least 1 mm.

19. The method of claim 18, wherein the fluid-carrying vessel is a gas-carrying vessel.

20. The method of claim 19, wherein the gas-carrying vessel is a bronchus.

21. The method of claim 18, further comprising generating the plasma flow, wherein a substantial portion of the flow has a temperature of least 11 kK.

* * * * *